(12) United States Patent
Falkenstein et al.

(10) Patent No.: US 11,814,409 B2
(45) Date of Patent: Nov. 14, 2023

(54) FC-RECEPTOR BASED AFFINITY CHROMATOGRAPHY

(71) Applicant: Hoffmann-La Roche Inc., Nutley, NJ (US)

(72) Inventors: Roberto Falkenstein, Munich (DE); Hubert Hertenberger, Weilheim (DE); Petra Rueger, Penzberg (DE); Tilman Schlothauer, Penzberg (DE)

(*) Notice: Subject to any disclaimer, the term of this patent is extended or adjusted under 35 U.S.C. 154(b) by 507 days.

(21) Appl. No.: 16/258,294

(22) Filed: Jan. 25, 2019

(65) Prior Publication Data

US 2019/0276492 A1 Sep. 12, 2019

Related U.S. Application Data

(63) Continuation of application No. 14/378,808, filed as application No. PCT/EP2013/052932 on Feb. 14, 2013, now abandoned.

(30) Foreign Application Priority Data

Feb. 15, 2012 (EP) .................................... 12155630

(51) Int. Cl.
| | | |
|---|---|---|
| C07K 1/22 | (2006.01) |
| B01D 15/16 | (2006.01) |
| B01D 15/38 | (2006.01) |
| B01J 20/289 | (2006.01) |
| B01J 20/32 | (2006.01) |
| C07K 16/06 | (2006.01) |
| C07K 16/28 | (2006.01) |
| B01J 39/26 | (2006.01) |
| G01N 33/68 | (2006.01) |

(52) U.S. Cl.
CPC .............. *C07K 1/22* (2013.01); *B01D 15/168* (2013.01); *B01D 15/3809* (2013.01); *B01J 20/289* (2013.01); *B01J 20/3204* (2013.01); *B01J 20/3206* (2013.01); *B01J 20/3219* (2013.01); *B01J 20/3274* (2013.01); *B01J 39/26* (2013.01); *C07K 16/065* (2013.01); *C07K 16/2866* (2013.01); *G01N 33/6854* (2013.01)

(58) Field of Classification Search
CPC .... C07K 1/22; C07K 14/70535; C07K 16/00; B01D 15/168
See application file for complete search history.

(56) References Cited

U.S. PATENT DOCUMENTS

| | | | |
|---|---|---|---|
| 4,676,980 A | 6/1987 | Segal et al. |
| 4,737,456 A | 4/1988 | Weng et al. |
| 4,816,567 A | 3/1989 | Cabilly et al. |
| 5,208,020 A | 5/1993 | Chari et al. |
| 5,416,064 A | 5/1995 | Chari et al. |
| 5,500,362 A | 3/1996 | Robinson et al. |
| 5,571,894 A | 11/1996 | Wels et al. |
| 5,587,458 A | 12/1996 | King et al. |
| 5,591,828 A | 1/1997 | Bosslet et al. |
| 5,623,053 A * | 4/1997 | Gastinel ........... C07K 14/70535 |
| | | | 435/69.1 |
| 5,624,821 A | 4/1997 | Winter et al. |
| 5,635,483 A | 6/1997 | Pettit et al. |
| 5,648,237 A | 7/1997 | Carter |
| 5,648,260 A | 7/1997 | Winter et al. |
| 5,658,570 A | 8/1997 | Newman et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,750,373 A | 5/1998 | Garrard et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,877,296 A | 3/1999 | Hamann et al. |
| 5,959,177 A | 9/1999 | Hein et al. |
| 6,040,498 A | 3/2000 | Stomp et al. |
| 6,075,181 A | 6/2000 | Kucherlapati et al. |

(Continued)

FOREIGN PATENT DOCUMENTS

| | | |
|---|---|---|
| EP | 0 425 235 B1 | 9/1996 |
| JP | 2017104130 A | 6/2017 |

(Continued)

OTHER PUBLICATIONS

Leach et al. Isolation from human placenta of the IgG transporter, FcRn, and localization to the syncytiotrophoblast: implications for maternal-fetal antibody transport. J Immunol. Oct. 15, 1996;157(8):3317-22. (Year: 1996).*

Yao et al. "Intein-mediated biotinylation of proteins and its application in a protein microarray" J. Am Chem. Soc. 2002, 124, 8768-8769 (Year: 2002).*

Canadian office action, dated Feb. 9, 2021, in the related Canadian Appl. No. 2,860,600.

Wozniak-Knopp et al., "Stabilisation of the Fc fragment of human IgG1 by engineered intradomain disulfide bonds," PLoS ONE, vol. 7 Issue 1, pp. e30083, Jan. 17, 2012.

(Continued)

*Primary Examiner* — Daniel E Kolker
*Assistant Examiner* — James L Rogers

(57) ABSTRACT

Herein is reported the use of an immobilized non-covalent complex of a neonatal Fc receptor (FcRn) and beta-2-microglobulin (b2m) as affinity chromatography ligand in general and, for example, for the determination of the in vivo half-live of an antibody by determining the ratio of the retention times of the antibody and a reference antibody.

16 Claims, 12 Drawing Sheets

Specification includes a Sequence Listing.

(56) References Cited

U.S. PATENT DOCUMENTS

| | | |
|---|---|---|
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,248,516 B1 | 6/2001 | Winter et al. |
| 6,267,958 B1 | 7/2001 | Andya et al. |
| 6,417,429 B1 | 7/2002 | Hein et al. |
| 6,420,548 B1 | 7/2002 | Vezina et al. |
| 6,602,684 B1 | 8/2003 | Umana et al. |
| 6,630,579 B2 | 10/2003 | Chari et al. |
| 6,737,056 B1 | 5/2004 | Presta |
| 6,946,292 B2 | 9/2005 | Kanda et al. |
| 6,982,321 B2 | 1/2006 | Winter |
| 7,041,870 B2 | 5/2006 | Tomizuka et al. |
| 7,087,409 B2 | 8/2006 | Barbas, III et al. |
| 7,125,978 B1 | 10/2006 | Vezina et al. |
| 7,189,826 B2 | 3/2007 | Rodman |
| 7,332,581 B2 | 2/2008 | Presta |
| 7,498,298 B2 | 3/2009 | Doronina et al. |
| 7,521,541 B2 | 4/2009 | Eigenbrot et al. |
| 7,527,791 B2 | 5/2009 | Adams et al. |
| 8,198,409 B2 | 6/2012 | Sato |
| 8,313,913 B2 | 11/2012 | Nakamura et al. |
| 9,096,651 B2 | 8/2015 | Igawa et al. |
| 2002/0004587 A1 | 1/2002 | Miller et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0072290 A1* | 4/2004 | Umana ............... C07K 16/00 435/69.1 |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0031613 A1 | 2/2005 | Nakamura et al. |
| 2005/0079574 A1 | 4/2005 | Bond |
| 2005/0119455 A1 | 6/2005 | Fuh et al. |
| 2005/0123546 A1 | 6/2005 | Umana et al. |
| 2005/0175606 A1 | 8/2005 | Huang et al. |
| 2005/0260186 A1 | 11/2005 | Bookbinder et al. |
| 2005/0266000 A1 | 12/2005 | Bond |
| 2006/0025576 A1 | 2/2006 | Miller et al. |
| 2006/0104968 A1 | 5/2006 | Bookbinder et al. |
| 2007/0061900 A1 | 3/2007 | Murphy et al. |
| 2007/0117126 A1 | 5/2007 | Sidhu et al. |
| 2007/0134759 A1 | 6/2007 | Nishiya et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2008/0241884 A1 | 10/2008 | Shitara et al. |
| 2009/0002360 A1 | 1/2009 | Chen et al. |
| 2010/0111967 A1 | 5/2010 | Baehner et al. |
| 2011/0111406 A1 | 5/2011 | Igawa et al. |
| 2013/0084648 A1 | 4/2013 | Bolton et al. |
| 2013/0131319 A1 | 5/2013 | Igawa et al. |

FOREIGN PATENT DOCUMENTS

| | | | |
|---|---|---|---|
| WO | 9301161 A1 | 1/1993 | |
| WO | 93/08829 A1 | 5/1993 | |
| WO | 93/16185 A1 | 8/1993 | |
| WO | 94/11026 A2 | 5/1994 | |
| WO | 94/29351 A1 | 12/1994 | |
| WO | 96027011 A1 | 9/1996 | |
| WO | 9632478 A1 | 10/1996 | |
| WO | 1997/30087 A1 | 8/1997 | |
| WO | 1998/58964 A1 | 12/1998 | |
| WO | 1999/22764 A1 | 5/1999 | |
| WO | 99/51642 A1 | 10/1999 | |
| WO | 2000/61739 A1 | 10/2000 | |
| WO | 2001/29246 A1 | 4/2001 | |
| WO | 2003/011878 A2 | 2/2003 | |
| WO | 2004/056312 A2 | 7/2004 | |
| WO | WO-2005047327 A2 * | 5/2005 | ............ A61P 35/00 |
| WO | 2005/053742 A2 | 6/2005 | |
| WO | 2006/029879 A2 | 3/2006 | |
| WO | 2006031370 A2 | 3/2006 | |
| WO | 2006/044908 A2 | 4/2006 | |
| WO | 2006121168 A1 | 11/2006 | |
| WO | 2008/077546 A1 | 7/2008 | |
| WO | 2009/080252 A1 | 7/2009 | |
| WO | 2009/080253 A1 | 7/2009 | |
| WO | 2009/080254 A1 | 7/2009 | |
| WO | 2009086320 A1 | 7/2009 | |
| WO | 2010045193 A1 | 4/2010 | |
| WO | WO-2010048313 A2 * | 4/2010 | ............... C07K 1/22 |
| WO | 2010/112193 A1 | 10/2010 | |
| WO | 2010/115589 A1 | 10/2010 | |
| WO | 2010/136172 A1 | 12/2010 | |
| WO | 2010/145792 A1 | 12/2010 | |
| WO | 2010/145793 A1 | 12/2010 | |
| WO | 2011122011 A2 | 10/2011 | |
| WO | 2011159877 A2 | 12/2011 | |
| WO | 2013087911 A1 | 6/2013 | |
| WO | 2014009465 A1 | 1/2014 | |
| WO | 2014131712 A1 | 9/2014 | |
| WO | 2015140126 A1 | 9/2015 | |
| WO | 2015175874 A2 | 11/2015 | |
| WO | 2016071376 A2 | 5/2016 | |

OTHER PUBLICATIONS

Adamski et al., "Expression of the Fc receptor in the mammary gland during lactation in the marsupial *Trichosurus vulpecula* (brushtail possum)," Molecular Immunology, Jun. 1, 2000, 37(8):435-444.

Coffey, "pH Gradient Elution for Improved Separation of Monoclonal Antibody Charge Variants," https://www.agilent.com/cs/library/applications/5990-9629EN.pdf, Aug. 1, 2013.

Ahouse et al., "Mouse MHC class I-like Fc receptor encoded outside the MHC," J Immunol Dec. 1, 1993, 151(11) 6076-6088.

Datta-Mannan et al., "FcRn Affinity-Pharmacokinetic Relationship of Five Human lgG4 Antibodies Engineered for Improved In Vitro FcRn Binding Properties in Cynomolgus Monkeys," Drug Metabolism and Disposition Aug. 2012, 40 (8) 1545-1555.

Kacskovics et al., "Cloning and characterization of the dromedary (Camelus dromedarius) neonatal Fc receptor (drFcRn)," Dev Comp Immunol. 2006;30(12):1203-15.

Kacskovics et al., "Cloning and characterization of the bovine MHC class I-like Fc receptor," J Immunol. Feb. 15, 2000;164(4):1889-97.

Kandil et al., "Structural and phylogenetic analysis of the MHC class I-like Fc receptor gene," J Immunol Jun. 1, 1995, 154 (11) 5907-5918.

Martin et al., "Characterization of the 2:1 Complex between the Class I MHC-Related Fc Receptor and Its Fc Ligand in Solution," Biochemistry, Sep. 3, 1999, V. 38, pp. 12639-12647.

Mayer et al., "edistribution of the sheep neonatal Fc receptor in the mammary gland around the time of parturition in ewes and its localization in the small intestine of neonatal lambs," Immunology. Nov. 2002; 107(3): 288-296.

Raghavan et al., "Effects of receptor dimerization on the interaction between the class I major histocompatibility complex-related Fc receptor and IgG," PNAS Nov. 21, 1995 92 (24) 11200-11204.

Schnulle et al., "Sequence and expression of the FcRn in the porcine mammary gland," Vet Immunol Immunopathol. Feb. 10, 2003;91(3-4):227-31.

Simister et al., "An Fc receptor structurally related to MHC class I antigens," Nature. Jan. 12, 1989;337(6203):184-7.

Story et al., "A major histocompatibility complex class I-like Fc receptor cloned from human placenta: possible role in transfer of immunoglobulin G from mother to fetus," J Exp Med. Dec. 1, 1994;180(6):2377-81.

Turkova, "Affinity Chromatography," Journal of Chromatography Library, vol. 12, 1978.

Vaughn et al., "High-Affinity Binding of the Neonatal Fc Receptor to Its IgG Ligand Requires Receptor Immobilization," Biochemistry Aug. 5, 1997, vol. 36, No. 31, pp. 9374-9380.

(56) References Cited

OTHER PUBLICATIONS

The U.S. office actions, dated Dec. 19, 2018 and dated May 28, 2019, in the related U.S. Appl. No. 15/271,091.
The U.S. office actions, dated Dec. 4, 2018 and dated Apr. 15, 2019, in the related U.S. Appl. No. 15/586,679.
The English translation of the Korean office action, dated Jun. 28, 2019, in the related Korean Appl. No. 10-2014-7022694.
Akilesh et al., "Neonatal FcR Expression in Bone Marrow-Derived Cells Functions to Protect Serum IgG from Catabolisml" J Immunol 179:4580-4588 ( 2007).
Brambell et al. et al., "A Theoretical Model of y-Globulin Catabolism" NATURE 203:1352-1354 (1964).
Brambell et al., "Nutrition of the foetus and the newly born" Proc. Nutr. Soc 28:35-41 (1969).
Chaudhury et al., "The Major Histocompatibility Complex—related Fc Receptor for IgG (FcRn) Binds Albumin and Prolongs Its Lifespan" J. Exp. Med. 197:315-322 (2003).
The International Search Report and Written Opinion, dated Jun. 5, 2015, in the related PCT Application No. PCT/EP2015/055482.
Ding et al., "ABT-874, a fully human monoclonal anti-IL-12/IL-23 antibody for the potential treatment of autoimmune diseases" Curr. Opin. Investig. Drugs 9:515-522 (2008).
Edelman et al., "Antibody structure and molecular immunology" J Immunol 34:1-22 (1991).
Faber et al., "Three-dimensional structure of a human Fab with high affinity for tetanus toxoidl" Immunotechnology 3:253-270 (1998).
Gandhi et al., "Anti-p40 antibodies ustekinumab and briakinumab: blockade of interleukin-12 and interleukin-23 in the treatment of psoriasis" Semin Cutan Med Surg. Mar. 2010;29(1):48-52.
Ghetie and Ward, "Multiple Roles for the Major Histocompatibility Complex Class I-Related Receptor FcRn" Ann Rev Immunol 18:739-766 (2000).
Goebl et al., "Neonatal Fc Receptor Mediates Internalization of Fc in Transfected Human Endothelial Cells" Mol. Biol. Cell 19:5490-5505 (2008).
Hess et al., "GROMACS 4: Algorithms for Highly Efficient, Loas-Balanced, and Scalable Molecular Simulation" J. Chem. Theory Comput. 4:435-447 (2008).
Jorgensen et al., "Development and Testing of the OPLS All-Atom Force Field on Conformational Energicts and Properties of Organic Liquids" J. Am. Chem. Soc. 118:11225-11236 (1996).
Kortkhonjia et al., "Probing antibody internal dynamics with fluorescence anisotropy and molecular dynamics simulations" mAbs 5:306-322 (2013).
Li et al., "DelPhi: a comprehensive suite for DelPhi software and associated resources" BMC. Biophys. 5(9) (2012).
Lima et al., "Expert Opinion on Biological Therapy, Briakinumab" Expert. Opin. Biol. Ther. 9:1107-1113 (2009).
Luo et al., "Structural Basis for the Dual Recognition of IL-12 and IL-23 by Ustekinumab" J. Mol. Biol. 402:797-812. (2010).
Martin et al., "Crystal structure at 2.8 A of an FcRn/heterodimeric Fc complex: mechanism of pH-dependent binding" Mol Cell 7(4):867-877 (Apr. 2001).
Montoyo et al., "Conditional deletion of the MHC class I-related receptor FcRn reveals the sites of IgG homeostasis in mice" PNAS 106:2788-2793 (2009).
Ober et al. "Exoc tosis of IgG as mediated by the receptor. FcRn: an Analysis at the Single-Molecule Level" Proc Natl Acad Sci U.S.A. 101 (30):11076-11081. (Jul. 2004).
Ober et al., "Visualizing the Site and Dynamics of IgG Salvage by the MHC Class I-Related Receptor, FcRnI" J Immunol 172:2021-2029 (2004).
Olafsen, T. Antibody Engineering—Methods in Molecular Biology "Fc Engineering: Serum Half-Life Modulation Through FcRn Binding" Humana Press.:537-556 (2012).
Petkova et al., "Enhanced half-life of genetically engineered human IgG1 antibodies in a humanized FcRn mouse model: potential application in humorally mediated autoimmune disease" International Immunology. 18:1759-1769 (2006).

Reff et al., "A review of modifications to recombinant antibodies: attempt to increase efficacy in oncology applications" Crit. Rev. Oncol. Hematol 40:25-35 (2001).
Rodewald et al., "ph-dependent binding of immunoglobulins to intestinal cells of the neonatal rat" J Cell Biol 71:666-669 (Nov. 1976).
Roopenian et al., "The MHC Class I-like IgG receptor controls perinatal IgG transport, IgG lionteoqthk_ and fate of IgG-Fc-coupled drugs" J Immunol 170(7):3528-3533 (Apr. 2003).
Ropeenian, "Human FcRn Transgenic Mice for Pharmacokinetic Evaluation of Therapeutic Antibodies" Methods Mol. Biol. 602:93-104 (2010).
Sanchez et al., "Stoichiometry of the Interaction between the Major Histocompatibility Complex-Related Fc Receptor and Its Fc Ligand" Biochemistry 38:9471-9476 (1999).
Fraczewski and Rudnicka, "Briakinumab for the Treatment of Plaque Psoriasis" BioDrugs 26:9-20 (2012).
Waldmann and Strober, "Metabolism of Immunoglobulins" Prog. Allergy 13: 1-110 (1969).
Weber and Keam, "Ustekinumab• Adis Drug Profile" BioDrugs 23:53-61 (2009).
Weger et al., "Current status and new developments in the treatment of psoriasis and psoriatic arthritis with biological agents" BJP 160:810-820 (2010).
Zalevsky et al., "Enhanced antibody half-life improves in vivo activity" Nat. Biotechnol 28:157-159 (2010).
Zhu et al., "Population Pharmacokinetic Modeling of Ustekinumab, a Human Monoclonal Antibody Targeting IL-12/23p40, in Patients With Moderate to Severe Plaque Psoriasis" J. Clin. Pharmacol. 49:162-175 (2009).
Brazilian office action, dated Aug. 13, 2020, in the related Brazilian Appl. No. BR112017006178-3.
U.S. office action, dated Oct. 30, 2020, in the related U.S. Appl. No. 15/271,091.
The Canadian office action, dated Nov. 21, 2019, in the related Canadian Appl. No. 2,860,600.
The Brazilian office action, dated Dec. 9, 2019, in the related Brazilian Appl. No. BR112014018005-9.
U.S. office actions, dated Nov. 20, 2019 and dated Jun. 18, 2020, in the related U.S. Appl. No. 15/271,091.
U.S. office actions, dated Nov. 29, 2019 and dated Mar. 4, 2020, in the related U.S. Appl. No. 15/586,679.
Cui et al., "Chemically Programmed Bispecific Antibodies That Recruit and Activate T Cells" Journal of Biological Chemistry 287 (34):28206-28214 (2012).
Garcia-Bennett et al., "In search of the Holy Grail: Folate-targeted nanoparticles for cancer therapy" Biochem Pharma 81:976-984 (2011).
Kopantzev et al., "Differences in gene expression levels between eariy and later stages of human lung development are opposite to those between normal lung tissue and non-small lung cell carcinoma" Lung Cancer 62(1):22-34 (2008).
Kortt et al., "Single-chain Fv fragments of anti-neuraminidase antibody NC10 containing five-and ten-residue linkers form dimers and with zero-residue linker a trimer" Protein Eng 10(4):423-433 (Apr. 1997).
Agilent Technologies, Inc., "pH Gradient Elution for Improved Separation of Monoclonal Antibody Charge Variants", Aug. 1, 2013.
Topalian et al., "Safety, Activity, and Immune Correlates of Anti-PD-1 Antibody in Cancer" N Engl J Med 366(26):2443-2454 (2012).
Chinese Office Action, dated Jun. 23, 2020, in the related Chinese Patent Appl. No. 201580060466.3.
The Russian Office Action, dated Oct. 29, 2018, in the related Russian Appl. No. 2016137932/10(059948).
The English translation of the Japanese Office Action, dated Jan. 8, 2019, in the related Japanese Appl. No. 2017-500408.
Kozlov I. G. Monoclonal antibodies are a new era in pharmacology and therapy. // Lechebnoe delo.—2006.—n. 1, pp. 26-31. (English abstract included.).
The English translation of the Chinese Office Action, dated Feb. 25, 2019, in the related Chinese Patent Appl. No. 201580015172.9.

(56) References Cited

OTHER PUBLICATIONS

The European Communication, dated Mar. 15, 2019, in the related European Patent Appl. No. 15710178.3.
The Russian Office Action, dated Apr. 23, 2019, in the related Russian Appl. No. 2017117856(030876).
The International Search Report and Written Opinion, dated May 11, 2016, in the related PCT Appl. No. PCT/EP2015/075656.
Dall'Acqua et al., "Increasing the affinity of a human IgG1 for the neonatal Fc receptor: biological consequences" J Immunol 169(9):5171-5180 (Nov. 1, 2002).
Dall'Acqua et al., "Properties of human IgGls engineered for enhanced binding to the neonatal Fc receptor (FcRn)" J Biol Chem 281(33):23514-23524 (Aug. 2006).
Firan et al., "The MHC class I-related receptor, FcRn, plays an essential role in the maternofetal transfer of y-globulin in humans" INTERNATIONALIMMUNOLOGY 13(8)1993-1002 (2001).
Medesan et al., "Localization of the site of the IgG molecule that regulates maternofetal transmission in mice" Eur J Immunol 26(10):2533-2536 (Oct. 1996).
Roopenian et al. "FcRn: the neonatal Fc receptor comes of age" Nat Rev/Immunol 7:715-725 (Sep. 2007).
The English translation of the Japanese office action, dated Aug. 3, 2021, in the related Japanese Appl. No. 2020-129979.
The English translation of the Decision to Grant a Patent, dated Feb. 8, 2022, in the related Japanese Appl. No. 2020-129979.
Atwell et al., "Stable Heterodimers from Remodeling the Domain Interface of a Homodimer using a Phage Dispaly Library" J. Mol. Biol. 270:26-35 (1997).
Darter, P., et al., "'Knobs-into-holes' provides a rational design strategy for engineering antibody CH3 domains for heavy chain heterodimerization" IMMUNOTECHNOLOGY 2(1):73 (Jan. 1996).
Clackson et al., "Making antibody fragments using phage display libraries" NATURE 352:624-628 (Aug. 15, 1991).
Datta-Mannan et al., "Monoclonal antibody clearance: impact of modulating the interaction of IgG with the neonatal Fc receptor," J. Biol. Chem. 282 (3): 1709-1717, 2007.
Datta-Mannan et al., "Aberrant bispecific antibody pharmacokinetics linked to liver sinusoidal endothelium clearance mechanism in cynomolgus monkeys," MAbs 8(5):969-982, (2016).
Datta-Mannan, Amita et al., "Balancing charge in the complementarity-determining regions of humanized mAbs without affecting pI reduces non-specific binding and improves the pharmacokinetics" MAbs 7(3):483-493, (2015).
Datta-Mannan et al., "The interplay of non-specific binding, target-mediated clearance and FcRn interactions on the pharmacokinetics of humanized antibodies" MABS 7(6):1084-1093, (2015).
Hotzel et al., "A strategy for risk mitigation of antibodies with fast clearance" MABS 4(6):753-760 (2012).
Kraft., "Heparin chromatography as an in vitro predictor for antibody clearance rate through pinocytosis," MABS 12 (i): e1683432, 9 pages, 2020.
Martin et al., "Peer Reviewed: Nanomaterials in Analytical Chemistry" Analytical Chemistry News & Features 70:322A-327A (May 1, 1998).
Merchant et al., "An efficient route to human bispecific IgG" Nat. Biotechnol. 16(7):677-681 (1998).
Neuber et al., "Characterization and screening of IgG binding to the neonatal Fc receptor" MABS 6(4):928-942 (2014).
Portolano, S., et al., Lack of promiscuity in autoantigen-specific H and L chain combinations as revealed by human H and L chain 'roulette' J. Immunol. 150(3):880-887 (Feb. 1, 1993).
Ridgway et al., "'Knobs-into-holes' Engineering of Antibody CH3 Domains for Heavy Chain Heterodimerization" Protein Eng. 9(7):617-621 (1996).
Schoch et al., "Charge-mediated influence of the antibody variable domain on FcRn-dependent pharmacokinetics" PNAS 112(19):5997-6002 (2015).
Stracke et al., "A novel approach to investigate the effect of methionine oxidation on pharmacokinetic properties of therapeutic antibodies" MABS 6:1229-1242 (2014).

The International Search Report and Written Opinion for PCT/EP2018/060536 dated Jul. 12, 2018.
The U.S. office action, dated Jun. 27, 2022, in U.S. Appl. No. 16/657,753.
Yamane-Ohnuki, N., et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yazaki et al., "Expression of Recombinant Antibodies in Mammalian Cell Lines" Methods in Molecular Biology 248:255-68 (2004).
Zhu, X., et al., "MHC Class I-Related Neonatal Fc Receptor for IgG Is Functionally Expressed in Monocytes, Intestinal Macrophages, and Dendritic Cells," J. Immunol. 166 (2001) 3266-3276.
King et al., "Monoclonal Antibody Conjugates of Doxorubicin Prepared with Branched Peptide Linkers: Inhibition of Aggregation by Methoxytriethyleneglycol Chains" J Med Chem 45(19 Suppl 4336-43(2002).
Klimka, A., et al., "Human anti-CD30 recombinant antibodies by guided phage antibody selection using cell panning," Br. J. Cancer 83 (2000) 252-260.
Kohler and Milstein, "Continuous cultures of fused cells secreting antibody of predefined specificity" Nature 256:495-497 (Aug. 7, 1975).
Kostelny et al., "Formation of a bispecific antibody by the use of leucine zippers" J Immunol. 148(5):1547-1553 (1992).
Kozbor et al., "A human hybrid myeloma for production of human monoclonal antibodies" J Immunol 133(6):3001-3005 (Dec. 1984).
Kratz, F., et al., "Prodrugs of anthracyclines in cancer chemotherapy" Curr Med Chem 13(5):477-523 (Mar. 1, 2006).
Lee et al., "Bivalent antibody phage display mimics natural immunoglobulin" J Immunol Methods 284(1-2):119-132 (2004).
Lee et al., "High-affinity human antibodies from phage-displayed synthetic Fab libraries with a single framework scaffold" J Mol Biol 340(5):1073-1093 (2004).
Li, H., et al., "Optimization of humanized IgGs in glycoengineered Pichia pastoris" Nat Biotechnol 24(2):210-215 (Feb. 1, 2006).
Li et al., "Human antibodies for immunotherapy development generation via a human B cell hybridoma technology" Proc Natl Acad Sci U S A 103(10):3557-62 (2006).
Lode et al., "Targeted Therapy with a Novel Enediyene Antibiotic Calicheamicin theta(I)1 Effectively Suppresses Growth and Dissemination of Liver Metastases in a Syngeneic Model of Murine Neuroblastoma" Cancer Res 58(14):2925-28 (1998).
Lonberg, N., et al., "Fully human antibodies from transgenic mouse and phage display platforms" Curr Opin Immunol 20(4):450-459 (Aug. 1, 2008).
Lonberg et al., "Human antibodies from transgenic animals" Nat Biotechnol 23(9):1117-25 (2005).
Marks and Bradbury Methods Mol Biol, Antibody Engineering "Selection of human antibodies from phage display libraries" Benny K. C. Lo,Humana Press, vol. 248:161-176 (2004).
Marks et al., "By-passing Immunization Human Antibodies from V-gene Libraries Displayed on Phage" J Mol Biol 222(3):581-97 (1991).
Mather, J., "Establishment and characterization of two distinct mouse testicular epithelial cell lines" Biol Reprod 23(1):243-252 (Aug. 1, 1980).
Mather et al., "Culture of Testicular Cells in Hormone-Supplemented Serum-Free Medium" Ann N Y Acad Sci 383:44-68 (1982).
McCafferty et al., "Phage antibodies: filamentous phage displaying antibody variable domains" Nature 348(6301):552-4 (1990).
Milstein and Cuello et al., "Hybrid hybridomas and their use in immunohistochemistry" Nature 305:537-540 (Oct. 6, 1983).
Morrison et al., "Chimeric Human Antibody Molecules: Mouse Antigen-Binding Domains with Human Constant Region Domains" P.N.A.S. USA 81:6851-6855 (1984).
Nagy et al., "Stability of cytotoxic luteinizing hormone-releasing hormone conjugate (AN-152) containing doxorubicin 14-O-hemiglutarate in mouse and human serum in vitro: Implications for the design of preclinical studies" Proc Natl Acad Sci U S A 97(2):829-34 (2000).

(56) References Cited

OTHER PUBLICATIONS

Ni, "Research progress and future perspectives in antibodomics and antibodomic drugs," HCAPLUS Accession humber 2006:1101736. Xiandai Mianyixue. 26(4):265-268 (2006) (Abstract Only) (3 pages)., pp. 3 (2006).
Noren et al., "A general method for site-specific incorporation of unnatural amino acids into proteins" Science 244(4901):182-188 (Apr. 14, 1989).
Ochi, A., et al., "Functional immunoglobulin M production after transfection of cloned immunoglobulin heavy and light chain genes into lymphoid cells" PNAS USA 80(20):6351-6355 (Oct. 1, 1983).
Okazaki et al., "Fucose depletion from human IgG1 oligosaccharide enhances binding enthalpy and association rate between IgG1 and FcgammaRIIIa" J Mol Biol 336(5):1239-1249 (Mar. 5, 2004).
Osbourn et al., "From rodent reagents to human therapeutics using antibody guided selection" Methods 36(1):61-8 (2005).
Padlan, E. et al., "A possible procedure for reducing the immunogenicity of antibody variable domains while preserving their ligand-binding properties" Mol Immunol 28(4-5):489-498 (Apr. 30, 1991).
Pluckthun et al. The Pharmacology of Monoclonal Antibodies Rosenburg and Moore (eds.), New York:Springer-Verlag, vol. 113:269-315 (1994).
Presta et al., "Humanization of an antibody directed against IgE" J Immunol 151(5):2623-2632 (Sep. 1, 1993).
Queen et al., "A humanized Antibody that Binds to the Interleukin 2 Receptor" P.N.A.S. USA 86:10029-10033 (1989).
Ravetch, J. et al., "Fc receptors" Annu Rev Immunol 9:457-492 (1991).
Remington, J., et al. Remington's Pharmaceutical Sciences (Table of Contents, total in 4 pages), OSOL, eds., 16th edition, Easton, PA:Mack Publishing Company, (1980).
Riechmann et al., "Reshaping human antibodies for therapy" Nature 322(6162):323-7 (1988).
Ripka, J., et al., "Two Chinese Hamster Ovary Glycosylation Mutants Affected in the Conversion of GDP-Mannose to GDP-Fucose" Arch Biochem Biophys 249(2):533-545 (Sep. 1, 1986).
Rosok et al., "A Combinatorial Library Strategy for the Rapid Humanization of Anticarcinoma BR96 Fab" J Biol Chem 271(37):22611-8 (1996).
Roux, K., et al., "Comparisons of the ability of human IgG3 hinge mutants, IgM, IgE, and IgA2, to form small immune complexes: a role for flexibility and geometry" J Immunol 161(8):4083-4090 (Oct. 15, 1998).
Sidhu et al., "Phage-displayed Antibody Libraries of Synthetic Heavy Chain Complementarity Determining Regions" J Mol Biol 338(2):299-310 (2004).
Sims et al., "A Humanized CD18 Antibody Can Block Function without Cell Destruction" J Immunol 151(4):2296-308 (1993).
Spiekermann, G.M., et al., "Receptor-mediated immunoglobulin G transport across mucosal barriers in adult life: functional expression of FcRn in the mammalian lung," J. Exp. Med. 196 (2002) 303-310.
Torgov et al., "Generation of an Intensely Potent Anthracycline by a Monoclonal Anitbody-Beta-Galactosidase Conjugate" Bioconjug Chem 16(3):717-21 (2005).
Traunecker et al., "Bispecific single chain molecules (Janusins) target cytotoxic lymphocytes on HIV infected cells" Embo J 10(12):3655-3659 (1991).
Tutt et al., "Trispecific F(ab')3 derivatives that use cooperative signaling via the TCR/CD3 complex and CD2 to activate and redirect resting cytotoxic T cells" J Immunol 147(1):60-69 (1991).
Urlaub et al., "Isolation of Chinese hamster cell mutants deficient in dihydrofolate reductase activity" Proc Natl Acad Sci U S A 77(7):4216-20 (1980).
Van Dijk, M., et al., "Human antibodies as next generation therapeutics" Curr Opin Chem Biol 5(4):368-374 (Aug. 1, 2001).
Vitetta et al., "Redesigning Nature's Poisons to Create Anti-Tumor Reagents" Science 238(4830):1098-104 (1987).
Vollmers et al., "The 'early birds': natural IgM antibodies and immune surveillance" Histol Histopathol 20(3):927-37 (2005).
Vollmers et al., "Death by Stress: Natural IgM-Induced Apoptosis" Methods Find Exp Clin Pharmacol 27(3):185-91 (2005).
Ward et al., "The Effector Functions of Immunoglobulins: Implications for Therapy." Therapeutic Immunology 2(2):77-94 (1995).
Winter et al., "Making Antibodies by Phage Display Technology" Annu Rev Immunol 12:433-55 (1994).
Wright, A., et al., "Effect of Glycosylation on Antibody Function: Implications for Genetic Engineering" Trends Biotechnol 15(1):26-32 (Jan. 1, 1997).
Akilesh, S., et al., "Podocytes use FcRn to clear IgG from the glomerular basement membrane," Proc. Natl. Acad. Sci. USA 105 (2008) 967-972.
Almagro, J.C. and Fransson, J., "Humanization of antibodies," Front. Biosci. 13 (2008) 1619-1633.
Baca, M., et al., "Antibody Humanization Using Monovalent Phage Display," J. Biol. Chem. 272 (1997) 10678-10684.
Boerner, P., et al., "Production of Antigen-Specific Human Monoclonal Antibodies From in Vitro-Primed Human Splenocytes," J. Immunol. 147 (1991) 86-95.
Brennan, M., et al., "Preparation of Bispecific Antibodies by Chemical Recombination of Monoclonal Immunoglobulin G1 Fragments," Science 229 (1985) 81-83.
Brodeur, B.R., et al., "Monoclonal Antibody Production Techniques and Applications," Marcel Dekker, Inc., New York (1987), pp. 51-63.
Bruggemann, M., et al., "Comparison of the Effector Functions of Human Immunoglobulins Using a Matched Set of Chimericantibodies," J. Exp. Med. 166 (1987) 1351-1361.
Carter, P., et al., "Humanizationofananti-p185HER2antibodyforhuman cancertherapy," Proc. Natl. Acad. Sci. USA 89 (1992) 4285-4289.
Chari, R.V., et al., "Immunoconjugates Containing Novel Maytansinoids: Promising Anticancer Drugs," Cancer Res. 52 (1992) 127-131.
Charlton, K.A., "Methods in Molecular Biology," vol. 248, Lo, B.K.C. (ed.), Humana Press, Totowa, NJ (2003), pp. 245-254.
Chothia, C. and Lesk, A.M., "Canonical Structures for the Hypervariable Regions of Immunoglobulins," J. Mol. Biol. 196 (1987) 901-917.
Chowdhury, P.S., "Engineering Hot Spots for Affinity Enhancement of Antibodies," Methods Mol. Biol. 207 (2008) 179-196.
Cragg, M.S. and M.J. Glennie, "Antibody specificity controls in vivo effector mechanisms of anti-CD20 reagents," Blood 103 (2004) 2738-2743.
Cragg, M.S., et al., "Complement-mediated lysis by anti-CD20 mAb correlates with segregation into lipid rafts," Blood 101 (2003) 1045-1052.
Cunningham, B.C. and Wells, J.A., "High-Resolution Epitope Mapping of hGH-Receptor Interactions by Alanine-Scanning Mutagenesis," Science 244 (1989) 1081-1085.
Dall'Acqua, W.F., et al., "Antibody humanization by framework shuffling," Methods 36 (2005) 43-60.
Dickinson, B.L., et al., "Bidirectional FcRn-dependent IgG transport in a polarized human intestinal epithelial cell line," J. Clin. Invest. 104 (1999) 903-911.
Dubowchik, G.M., et al., "Doxorubicin Immunoconjugates Containing Bivalent, Lysosomally-Cleavable Dipeptide inkages," Bioorg. & Med. Chem. Letters 12 (2002) 1529-1532.
Duncan, A.R. and Winter, G., "The binding site for C1q on IgG," Nature 322 (1988) 738-740.
Ellman, et al., Biosynthetic Method for Introducing Unnatural Amino Acids Site-Specifically into Proteins Meth. Enzym. 202 (1991) 301-336.
Fellouse, F.A., "Synthetic antibedks from iiour-amino-zicid code: A dominant role for tyrosine in antigen recognition," Proc. Natl. Acad. Sci. USA 101 (2004) 12467-12472.
Gazzano-Santoro, H., et al., "A non-radioactive complement-dependent cytotoxicity assay for anti-CD20 monoclonal antibody," J. Immunol. Methods 202 (1996) 163-171.
Gerngross, T.U., "Advances in the production of human therapeutic proteins in yeasts and filamentous fungi," Nat. Biotech. 22 (2004) 1409-1414.
Ghetie, V., et al., "Increasing the serum persistence of an IgG fragment by random mutagenesis," Nat. Biotechnol. 15 (1997) 637-640.

(56) References Cited

OTHER PUBLICATIONS

Graham, F.L., et al., "Characteristics of a Human Cell Line Transformed by DNA from Human Adenovirus Type 5," J. Gen Virol. 36 (1977) 59-74.
Griffiths, A.D., et al., "Human anti-self antibodies with high specificity from phage display libraries," EMBO J. 12 (1993) 725-734.
Gruber, M., et al., "Efficient tumor cell lysis mediated by a bispecific single chain antibody expressed in Escherichia coli," J. Immunol. 152 (1994) 5368-5374.
Guyer, R.L., et al., "Immunoglobulin Binding by Mouse Intestinal Epithelial Cell Receptors," J. Immunol. 117 (1976) 587-593.
Hellstrom, I., et al., "Strong antitumoractivities of IgG3 antibodies to a human melanoma-associated ganglioside," Proc. Natl. Acad. Sci. USA 82 (1985) 1499-1502.
Hellstrom, I., et al., "Antitumor effects of L6, and IgG2a antibody that reacts with most human carcinomas," Proc. Natl. Acad. Sci. USA 83 (1986) 7059-7063.
Hermanson, G.T., et al., "Antibody Modification and Conjugation," Bioconjugate Techniques, Academic Press (1996). (Two pages).
Hinman, L.M., et al., "Preparation and Characterization of Monoclonal Antibody Conjugates of the Calicheamicins: A Novel and Potent Family of Antitumor Antibiotics," Cancer Res. 53 (1993) 3336-3342.
Hinton, P.R., et al., "Engineered Human IgG Antibodies with Longer Serum Half-lives in Primates," J. Biol. Chem. 279 (2004) 6213-6216.
Hinton, P.R., et al., "An Engineered Human IgG1 Antibody with Longer Serum Half-Life," J. Immunol. 176 (2006) 346-356.
Holliger, P., et al., ""Diabodies": Smallbivalentandbispecificantibodyfragments," Proc. Natl. Acad. Sci. USA 90 (1993) 6444-6448.
Hoogenboom, H.R. and Winter, G., "By-passing Immunisation Human Antibodies from Synthetic Repertoires of Germline VH Gene Segments Rearranged in Vitro," J. Mol. Biol. 227 (1992) 381-388.
Hoogenboom, H.R., et al., "Overview of Antibody Phage-Display Technology and Its Applications," Methods in Molecular Biology 178 (2002) 1-37.
Hudson, P.J. et al., "Engineered antibodies," Nat. Med. 9 (2003) 129-134.
Idusogie, E.E., et al., "Mapping of the C1q Binding Site on Rituxan, a Chimeric Antibody with a Human IgG1 Fc," J. Immunol. 164 (2000) 4178-4184.
Israel, E.J., "Increased clearance of IgG in mice that lack beta 2-microglobulin: possible protective role of FcRn" Immunology 89 (1996) 573-578.
Jeffrey, S.C., et al., "Dipeptide-based highly potent doxorubicin antibody conjugates," Bioorg. Med. Chem. Lett. 16 (2006) 358-362.
Junghans, R.P. and Anderson, C.L., "The protection receptor for IgG catabolismis the β32-microglobulin-containing neonatal intestinal transport receptor," Proc. Natl. Acad. Sci. USA 93 (1996) 5512-5516.
Kabat, E.A., et al., "Sequences of Proteins of Immunological Interest," 5th ed. Public Health Service, National Institutes of Health, Bethesda, MD (1991), NIH Publication 91-3242.
Kam, N.W., et al., "Carbon nanotubes as multifunctional biological transporters and near-infrared agents for selective cancer cell destruction," Proc. Natl. Acad. Sci. USA 102 (2005) 11600-11605.
Kanda, Y., et al., "Comparison of Cell Lines for Stable Production of Fucose-Negative Antibodies With Enhanced ADCC," Biotechnol. Bioeng. 94 (2006) 680-688.
Kashmiri, S.V., et al., "SDR grafting a new approach to antibody humanization," Methods 36 (2005) 25-34.
Kim, H., et al., "Mapping of the Neonatal Fc Receptor in the Rodent Eye," Invest. Ophthalmol. Vis. Sci. 49 (2008) 2025-2029.
Kim et al., "Localization of the site of the murine IgG1 molecule that is involved in binding to the murine intestinal Fc receptor" Eur J Immunol 24(10):2429-2434 (1994).
Kindt et al. Kuby Immunology "Antigens and Antibodies Chapter 4" 6th ed edition, N.Y.:W.H. Freeman and Co,:p. 91 (2007).

* cited by examiner

AUC(0-672)

terminal half-life

SEQUENCE LISTING

<160> NUMBER OF SEQ ID NOS: 10

<210> SEQ ID NO 1
<211> LENGTH: 107
<212> TYPE: PRT
<213> ORGANISM: Homo sapiens

<400> SEQUENCE: 1

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Trp Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Glu Ser Thr Tyr Arg Trp Ser Val Leu Thr Val Leu His Gln Asp Trp
65                  70                  75                  80

Leu Asn Gly Lys Glu Tyr Lys Cys Lys Val Ser Asn Lys Ala Leu Pro
                85                  90                  95

Ala Pro Ile Glu Lys Thr Ile Ser Lys Ala Lys
            100                 105

<210> SEQ ID NO 2
<211> LENGTH: 106
<212> TYPE: PRT
<213> ORGANISM: Homo sapiens

<400> SEQUENCE: 2

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 4
<211> LENGTH: 326
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
```

```
                    100                 105                 110
Pro Val Ala Gly Pro Ser Val Phe Leu Phe Pro Lys Pro Lys Asp
            115                 120                 125
Thr Leu Met Ile Ser Arg Thr Pro Glu Val Thr Cys Val Val Asp
130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 5
<211> LENGTH: 377
<212> TYPE: PRT
<213> ORGANISM: Homo sapiens

<400> SEQUENCE: 5

Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Thr Cys Asn Val Asn His Lys Pro Ser Asn Thr Lys Val Asp Lys
                85                  90                  95
Arg Val Glu Leu Lys Thr Pro Leu Gly Asp Thr Thr His Thr Cys Pro
            100                 105                 110
Arg Cys Pro Glu Pro Lys Ser Cys Asp Thr Pro Pro Pro Cys Pro Arg
        115                 120                 125
Cys Pro Glu Pro Lys Ser Cys Asp Thr Pro Pro Pro Cys Pro Arg Cys
    130                 135                 140
```

-continued

```
Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
            165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 6
<211> LENGTH: 330
<212> TYPE: PRT
<213> ORGANISM: Homo sapiens

<400> SEQUENCE: 6

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Asp Lys Thr His Thr Cys Pro Pro Cys
            100                 105                 110

Pro Ala Pro Glu Phe Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

Val Val Val Asp Val Ser Gln Glu Asp Pro Glu Val Gln Phe Asn Trp
145                 150                 155                 160

Tyr Val Asp Gly Val Glu Val His Asn Ala Lys Thr Lys Pro Arg Glu
            165                 170                 175

Glu Gln Phe Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Gly Leu Pro Ser Ser Ile Glu Lys Thr Ile Ser Lys Ala Lys Gly
210                 215                 220

Gln Pro Arg Glu Pro Gln Val Tyr Thr Leu Pro Pro Ser Gln Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Arg Leu Thr Val Asp Lys Ser Arg Trp Gln Glu Gly Asn
290                 295                 300

Val Phe Ser Cys Ser Val Met His Glu Ala Leu His Asn His Tyr Thr
305                 310                 315                 320

Gln Lys Ser Leu Ser Leu Ser Leu Gly Lys
            325                 330

<210> SEQ ID NO 7
<211> LENGTH: 274
<212> TYPE: PRT
<213> ORGANISM: Homo sapiens

<400> SEQUENCE: 7

Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly

```
              180                 185                 190
Phe Ser Val Leu Thr Cys Ser Ala Phe Ser Phe Tyr Pro Pro Glu Leu
            195                 200                 205
Gln Leu Arg Phe Leu Arg Asn Gly Leu Ala Ala Gly Thr Gly Gln Gly
            210                 215                 220
Asp Phe Gly Pro Asn Ser Asp Gly Ser Phe His Ala Ser Ser Ser Leu
225                 230                 235                 240
Thr Val Lys Ser Gly Asp Glu His His Tyr Cys Cys Ile Val Gln His
            245                 250                 255
Ala Gly Leu Ala Gln Pro Leu Arg Val Glu Leu Glu Ser Pro Ala Lys
            260                 265                 270
Ser Ser

<210> SEQ ID NO 8
<211> LENGTH: 21
<212> TYPE: PRT
<213> ORGANISM: Artificial Sequence
<220> FEATURE:
<223> OTHER INFORMATION: HIS-AVITAG

<400> SEQUENCE: 8

His His His His His His Gly Leu Asn Asp Ile Phe Glu Ala Gln Lys
1               5                   10                  15
Ile Glu Trp His Glu
            20

<210> SEQ ID NO 9
<211> LENGTH: 99
<212> TYPE: PRT
<213> ORGANISM: Homo sapiens

<400> SEQUENCE: 9

Ile Gln Arg Thr Pro Lys Ile Gln Val Tyr Ser Arg His Pro Ala Glu
1               5                   10                  15
Asn Gly Lys Ser Asn Phe Leu Asn Cys Tyr Val Ser Gly Phe His Pro
            20                  25                  30
Ser Asp Ile Glu Val Asp Leu Leu Lys Asn Gly Glu Arg Ile Glu Lys
            35                  40                  45
Val Glu His Ser Asp Leu Ser Phe Ser Lys Asp Trp Ser Phe Tyr Leu
    50                  55                  60
Leu Tyr Tyr Thr Glu Phe Thr Pro Thr Glu Lys Asp Glu Tyr Ala Cys
65                  70                  75                  80
Arg Val Asn His Val Thr Leu Ser Gln Pro Lys Ile Val Lys Trp Asp
                85                  90                  95
Arg Asp Met

<210> SEQ ID NO 10
<211> LENGTH: 227
<212> TYPE: PRT
<213> ORGANISM: Artificial Sequence
<220> FEATURE:
<223> OTHER INFORMATION: Fc-Region

<400> SEQUENCE: 10

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
```

-continued

```
Ile Ser Arg Thr Pro Glu Val Thr Cys Val Val Val Asp Val Ser His
        35                  40              45
Glu Asp Pro Glu Val Lys Phe Asn Trp Tyr Val Asp Gly Val Glu Val
    50              55                  60
His Asn Ala Lys Thr Lys Pro Arg Glu Glu Gln Tyr Asn Ser Thr Tyr
65              70                  75                      80
Arg Val Val Ser Val Leu Thr Val Leu His Gln Asp Trp Leu Asn Gly
            85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
    130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
        210                 215                 220
Pro Gly Lys
225
```

FC-RECEPTOR BASED AFFINITY CHROMATOGRAPHY

This application claims priority to and is a continuation of pending U.S. patent application Ser. No. 14/378,808, filed Aug. 14, 2014, which in turn claims priority to National Stage Application of PCT/EP2013/052932, filed Feb. 14, 2013, which in turn claims priority from European Application No. 12155630.2, filed on Feb. 15, 2012. Each of these applications is hereby incorporated by reference herein in its entirety.

Herein is reported the use of an affinity chromatography column comprising immobilized human neonatal Fc receptor as affinity ligand and its use.

BACKGROUND

An immunoglobulin in general comprises two so called light chain polypeptides (light chain) and two so called heavy chain polypeptides (heavy chain) Each of the heavy and light chain polypeptides contains a variable domain (variable region) (generally the amino terminal portion of the polypeptide chain) comprising binding regions that are able to interact with an antigen. Each of the heavy and light chain polypeptides comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q).

The neonatal Fc receptor (FcRn) is also known as the MHC Class I-related receptor (for review see Ward, E. S. and Ober, R. J., Advances in Immunology 103 (2009) 77-115). Studies have not only shown that this receptor serves to regulate IgG levels and distribution throughout adult life (Ghetie, V., et al., Nat. Biotechnol. 15 (1997) 637-640; Israel, E. J., Immunology 89 (1996) 573-578; Junghans, R. P. and Anderson, C. L., Proc. Natl. Acad. Sci. USA 93 (1996) 5512-5516), but also that it has multiple other roles in diverse cell types and tissues (see e.g. Akilesh, S., et al., Proc. Natl. Acad. Sci. USA 105 (2008) 967-972; Dickinson, B. L., et al., J. Clin. Invest. 104 (1999) 903-911; Kim, H., et al., Invest. Ophthalmol. Vis. Sci. 49 (2008) 2025-2029; Spiekermann, G. M., et al., J. Exp. Med. 196 (2002) 303-310; Zhu, X., et al., J. Immunol. 166 (2001) 3266-3276). FCRn orthologs have been isolated from many species, including mouse, rat, man, sheep, cow, possum, pig, and camel (Adaniski, F. M., et al., Mol. Immunol. 37 (2000) 435-444; Ahouse, J. J., et al., J. Immunol. 151 (1993) 6076-6088; Kacskovics, I., et al., J. Immunol. 164 (2000) 1889-1897; Kacskovics, I., et al., Dev. Comp. Immunol. 30 (2006) 1203-1215; Kandil, E., et al., J. Immunol. 154 (1995) 5907-5918; Mayer, B., et al., Immunology 107 (2002) 288-296; Selanulle, P. M. and Hurley, W. L., Vet. Immunol. Immunopathol, 91 (2003) 227-231; Simister, N. E. and Mostov, K. E., Nature 337 (1989) 184-187; Story, C. M., et al., J. Exp. Med. 180 (1994) 2377-2381), indicating that this receptor is present in essentially all mammalian species. The multiple functions of FcRn are dependent on its ability to sort IgG away from lysosomal degradation within cells and release bound cargo during exocytic events at the plasma membrane (Ober, R. J., et al., Proc. Natl. Acad. Sci. USA 101 (2004) 11076-11081; Ober, R. J., et al., J. Immunol. 172 (2004) 2021-2029; Prabhat, P., et al., Proc. Natl. Acad. Sci. USA 104 (2007) 5889-5894). In addition, given the potential for modulating IgG trafficking pathways and behavior in vivo, the earlier report of engineering of antibodies to increase their half-life in mice (Ghetie et al., supra) has expanded into an area of intense interest in the biopharmaceutical industry (Dall'Acqua, W. F., et al., J. Biol. Chem. 281 (2006) 23514-23524; Hinton, P. R., et al., J. Biol. Chem. 279 (2004) 6213-6216; Hinton, P. R., et al., J. Immunol. 176 (2006) 346-356; Shields, R. L., et al., J. Biol. Chem. 276 (2001) 6591-6604).

In WO 2005/047327 neonatal Fc receptor (FcRn)-binding polypeptide variants, dimeric Fc binding proteins and methods related thereto are reported. Polypeptide variants with altered effector function are reported in WO 2006/031370. In WO 2009/041643 a method of modifying isoelectric point of antibody via amino acid substitution in CDR is reported. In WO 2010/048313 recombinant FcRn and variants thereof for purification of Fc-containing fusion proteins is reported. Magistrelli, G., et al., report robust recombinant FcRn production in mammalian cells enabling oriented immobilization for IgG binding studies (J. Immunol. Meth. in press, available online Dec. 9, 2011).

SUMMARY

One aspect as reported herein is the use of an immobilized non-covalent complex of a neonatal Fc receptor (FcRn) and beta-2-microglobulin (b2m) as affinity chromatography ligand.

It has been found that with the method/use as reported herein it is now possible to separate, isolate and characterize with respect to their in vivo properties closely related antibody species, i.e. differing in a single or a limited number of amino acid residues.

Thus, the different antibody species, i.e. one amino acid residue difference, isolated with the method as reported herein can be used to characterize/identify FcRn related half-life influencing amino acid positions.

Thus, with the method as reported herein it is possible to separate different variants of one parent antibody and to determine the specific ratio between these variants, which is not possible with the currently known methods as these only provide the sum of the modifications and not the individual species (i.e. for a mixture of parent and variant 1 and variant 2 and variant 1/2 the mass spectrometry provides for the total of variant 1 comprising molecules, i.e. variants comprising a single variation (1) and also those comprising also the second variation (1/2)).

This can be achieved by the combination of i) the immobilization on a chromatography support of recombinantly produced human FcRn in combination with recombinantly produced human beta 2 microglobulin and ii) a linear pH gradient.

It has been found that for the given conditions a wild-type IgG1 antibody has a retention time of about 42 to 49 minutes. In one embodiment an antibody or Fc-fusion protein comprising a wild type Fc-region of the IgG1 subclass has a retention time of about 45 minutes.

An antibody having a modified Fc-region with reduced FcRn binding has a retention time that is smaller, whereas an antibody having a modified Fc-region with enhanced FcRn binding has a retention time that is bigger. In one embodiment the non-covalent complex of a neonatal Fc receptor (FcRn) and beta-2-microglobulin (b2m) is hound to a solid phase. In one embodiment the solid phase is a chromatography material. In one embodiment the non-covalent complex of a neonatal Fc receptor (FcRn) and beta-2-microglobulin (b2m) is biotinylated and the solid phase is derivatized with streptavidin.

In one embodiment the use is in an affinity chromatography with a pH gradient. In one embodiment the pH gradient is from a first pH value to a second pH value whereby the first pH value is from about pH 3.5 to about pH 7.5 and the second pH value is from about pH 6.0 to about pH 9.5. In one embodiment the pH gradient is a gradient with increasing pH value or a gradient with decreasing pH value. In one embodiment the first pH value is about pH 5.5 and the second pH value is about pH 8.8 or the first pH value is about pH 7.4 and the second pH value is about pH 6.0.

In one embodiment the beta-2-microglobulin is from the same species as the FcRn.

In one embodiment the use is for the determination of the in vivo half-live of an antibody by determining the ratio of the retention times of the antibody and a reference antibody.

In one embodiment the use is for the separating of antibodies or fusion polypeptides comprising at least an Fc-region.

In one embodiment the use is for determining methionine oxidation of an antibody.

In one embodiment the use is for determining the oligomerization level of an antibody.

In one embodiment the use is for screening a library of modified antibodies or modified fusion polypeptides of a parent antibody or a parent fusion polypeptide which comprise at least an FcRn binding portion of an Fc-region for those modified antibodies or modified fusion polypeptides that have an altered binding affinity for FcRn compared to the parent antibody or parent fusion polypeptide.

In one embodiment the use is for identifying antibodies or fusion polypeptides that comprise at least an FcRn-binding portion of an Fc-region which exhibit altered binding to the neonatal Fc receptor.

In one embodiment the antibody is a monospecific antibody or antibody fragment of fusion polypeptide, or a bispecific antibody or antibody fragment of fusion polypeptide, or a trispecific antibody or antibody fragment of fusion polypeptide, or a tetraspecific antibody or antibody fragment of fusion polypeptide.

In one embodiment the use is for the removal of half antibodies from IgG preparations.

In one embodiment the use is for the removal of antibody aggregates and antibody oligomers from IgG preparations.

One aspect as reported herein is an Fc-region variant of human IgG1 isotype in which the amino acid at position 252 is changed from methionine to histidine and the amino acid at position 428 is changed from methionine to glutamic acid.

One aspect as reported herein is a method for selecting an antibody with a predetermined in vivo half-live wherein a chromatography is performed and an antibody is selected that has a retention time within a given retention time window relative to a wild-type IgG1.

DETAILED DESCRIPTION OF EMBODIMENTS OF THE INVENTION

Figure 1:
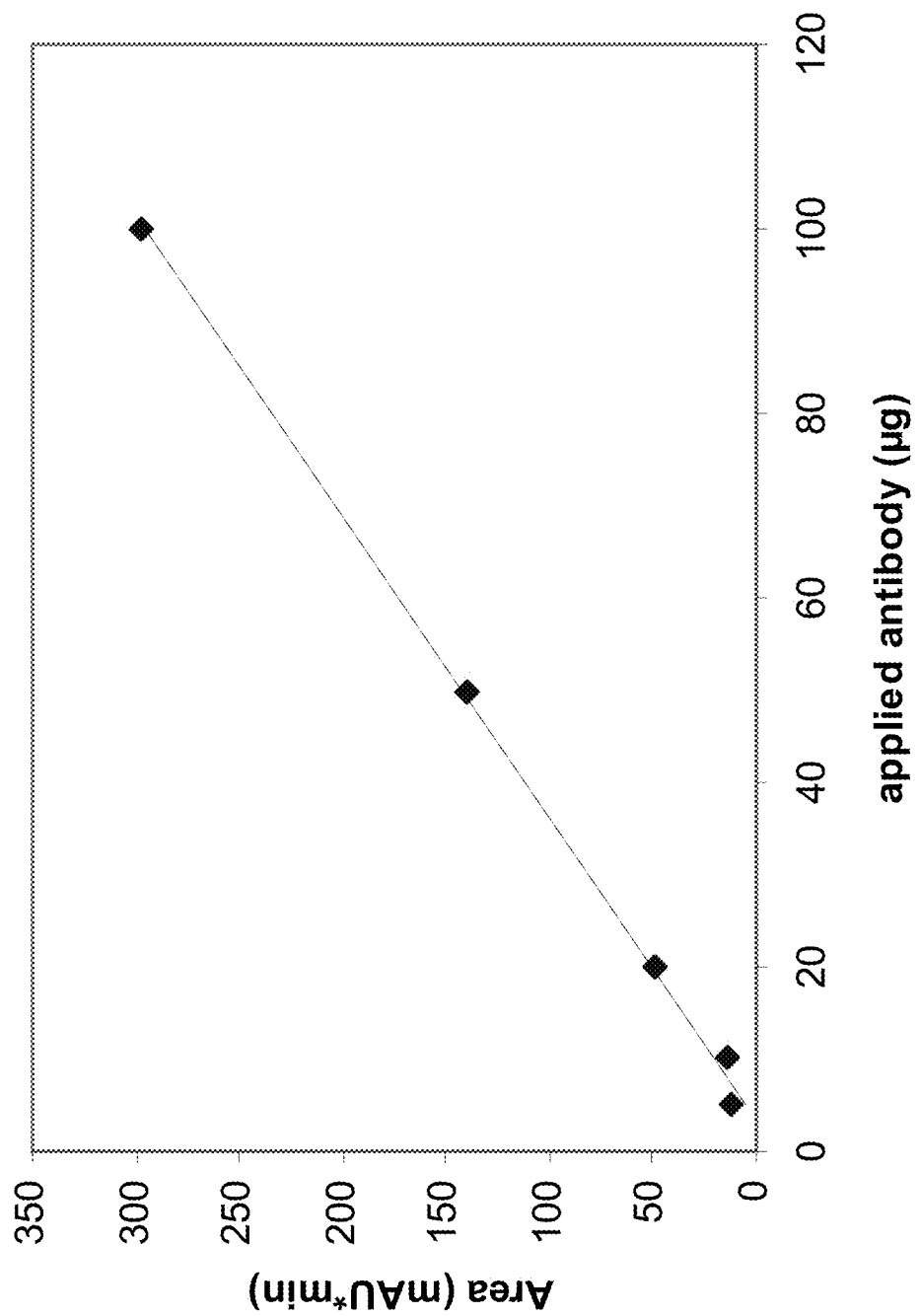
FIG. 1 Linearity of applied antibody and area under the curve of a chromatography using an FcRn column as reported herein.

The neonatal Fc receptor (FcRn) is important for the metabolic fate of IgG antibodies in vivo.

FcRn affinity chromatography can differentiate IgG samples by their peak area and retention time profile. It allows the analysis of the interaction between FcRn and IgG in vitro and can provide insight into the structural and functional integrity of therapeutic IgG regarding pharmacokinetics in vivo.

Thus, FcRn affinity chromatography of mutant and wild-type IgGs can be used as semi-quantitatively predictive of in vivo pharmacokinetics. Further, FcRn affinity chromatography can be used to monitor FcRn-IgG interaction, e.g. for IgG batch characterization or for comparability studies.

A standardized pH gradient FcRn affinity liquid chromatography method has been found with conditions closely resembling the mechanism of interaction between IgG and FcRn in vivo. Human FcRn was immobilized on the column as affinity ligand and a linear pH gradient e.g. from pH 5.5 to 8.8 was applied.

For example, analytical FcRn affinity chromatography allows identification and characterization of IgG samples and variants by peak pattern and retention time profile. The method can distinguish 1) the same IgG with different Fab fragments, 2) oxidized IgG forms from non-oxidized IgG forms, 3) aggregates from monomers, and 4) antibodies with variations in the Fc-region.

It has been found that changes in the FcRn affinity chromatography profile of variant IgGs (Fc-region variants) relative to the wild-type IgG are predictive of the in vivo pharmacokinetic profile. These results demonstrate that FcRn affinity chromatography is a useful new method for the characterization of FcRn-IgG interactions, of IgG integrity, and at most of an IgG as such.

I. Definitions

The term "about" denotes a range of +/−20% of the thereafter following numerical value. In one embodiment the term about denotes a range of +/−10% of the thereafter following numerical value. In one embodiment the term about denotes a range of +/−5% of the thereafter following numerical value.

The term "alteration" denotes the substitution, addition, or deletion of one or more amino acid residues in a parent antibody or fusion polypeptide comprising at least an FcRn binding portion of an Fc-region to obtain a modified antibody or fusion polypeptide.

The term "amino acid substitution" denotes the replacement of at least one existing amino acid residue with another different amino acid residue (replacing amino acid residue). The replacing amino acid residue may be a "naturally occurring amino acid residues" and selected from the group consisting of alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine F), proline (pro, P), serine (ser, S), threonine (thr, T), tryptophan (trp, W), tyrosine (tyr, Y), and valine (val, V).

The term "amino acid insertion" denotes the incorporation of at least one amino acid residue at a predetermined position in an amino acid sequence. In one embodiment the insertion will be the insertion of one or two amino acid residues. The inserted amino acid residue(s) can be any naturally occurring or non-naturally occurring amino acid residue.

The term "amino acid deletion" denotes the removal of at least one amino acid residue at a predetermined position in an amino acid sequence.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit FcRn-binding property.

The term "buffer substance" denotes a substance that when in solution can level changes of the pH value of the solution e.g. due to the addition or release of acidic or basic substances.

The term "CH2 domain" denotes the part of an antibody heavy chain polypeptide that extends approximately from EU position 231 to EU position 340 (EU numbering system according to Kabat). In one embodiment a CH2 domain has the amino acid sequence of SEQ ID NO: 1: APELLGG PSVFLFPPKP KDTLIMIISRTP EVTCVWDVS HEDPE- VKFNW YVIDGVEVHNA KTKPREEQ E STYRWSVLT VLHQDWLNGK EYKCKVSNKA LPAPIEKTIS KAK.

The term "CH3 domain" denotes the part of an antibody heavy chain polypeptide that extends approximately from EU position 341 to EU position 446. In one embodiment the CH3 domain has the amino acid sequence of SEQ ID NO: 2: GQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPG.

The term "class" of an antibody denotes the type of constant domain or constant region possessed by its heavy chain. There are five major classes of antibodies: IgA, IgD, IgE, IgG, and IgM, and several of these may be further divided into subclasses (isotypes), $IgG_1$, $IgG_2$, $IgG_3$, $IgG_4$, $IgA_1$, and $IgA_2$, The heavy chain constant domains that correspond to the different classes of immunoglobulins are called α, δ, ε, γ, and μ, respectively.

The term "Fc-region of human origin" denotes the C-terminal region of an immunoglobulin heavy chain of human origin that contains at least a part of the hinge region, the CH2 domain and the CH3 domain. In one embodiment, a human IgG heavy chain Fc-region extends from Cys226, or from Pro230, to the carboxyl-terminus of the heavy chain. In one embodiment the Fc-region has the amino acid sequence of SEQ ID NO: 10. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, Md. (1991), NIH Publication 91-3242.

The term "FcRn" denotes the human neonatal Fc-receptor. FcRn functions to salvage IgG from the lysosomal degradation pathway, resulting in reduced clearance and long half-life. The FcRn is a heterodimeric protein consisting of two polypeptides: a 50 kDa class I major histocompatibility complex-like protein (α-FcRn) and a 15 kDa β2-microglobulin (β2m). FcRn binds with high affinity to the C2-CH3 portion of the Fc domain of IgG. The interaction between IgG and FcRn is strictly pH dependent and occurs in a 1:2 stoichiometry, with one IgG binding to two FcRn molecules via its two heavy chains (Huber, et al., J. Mol. Biol. 230 (1993) 1077-1083), FcRn binding occurs in the endosome at acidic pH (pH<6.5) and IgG is released at the neutral cell surface (pH of about 7.4). The pH-sensitive nature of the interaction facilitates the FcRn-mediated protection of IgGs pinocytosed into cells from intracellular degradation by binding to the receptor within the acidic environment of endosomes. FcRn then facilitates the recycling of IgG to the cell surface and subsequent release into the blood stream upon exposure of the FcRn-IgG complex to the neutral pH environment outside the cell.

The term "FcRn binding portion of an Fc-region" denotes the part of an antibody heavy chain polypeptide that extends approximately from EU position 243 to EU position 261 and approximately from EU position 275 to EU position 293 and approximately from EU position 302 to EU position 319 and approximately from EU position 336 to EU position 348 and approximately from EU position 367 to EU position 393 and EU position 408 and approximately from EU position 424 to EU position 440, In one embodiment one or more of the following amino acid residues according to the EU numbering of Kabat are altered F243, P244, P245 P, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440 (EU numbering).

The term "full length antibody" denotes an antibody having a structure substantially similar to a native antibody structure or having heavy chains that contain an Fc-region as defined herein.

The term "hinge region" denotes the part of an antibody heavy chain polypeptide that joins the CH1 domain and the CH2 domain, e.g. from about position 216 to position about 230 according to the EU number system of Kabat. The hinge region is normally a dimeric molecule consisting of two polypeptides with identical amino acid sequence. The hinge region generally comprises about 25 amino acid residues and is flexible allowing the antigen binding regions to move independently. The hinge region can be subdivided into three domains: the upper, the middle, and the lower hinge domain (Roux, et al., J. Immunol 161 (1998) 4083).

The terms "host cell", "host cell line", and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "humanized" antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g. the CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-914 Exemplary CDRs (CDR-L1, CDR-L2, CDR-L3, CDR-H1, CDR-H2, and CDR-H13) occur at amino acid residues 24-34 of L1, 50-56 of L2, 89-97 of L3, 31-35B of H1, 50-65 of H2, and 95-102 of H3 (Kabat, E. A., et al., Sequences of Proteins of Immunological Interest, 5th ed. Public Health Service, National Institutes of Health, Bethesda. Md. (1991), NIH Publication 91-3242). With the exception of CDR1 in VH, CDRs generally comprise the amino acid residues that form the hypervariable loops. CDRs also comprise "specificity determining residues", or "SDRs", which are residues that contact antigen. SDRs are contained within regions of the CDRs called abbreviated-CDRs, a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (see Almagro, J. C. and Fransson, J., Front. Biosci. 13 (2008) 1619-1633). Unless otherwise indicated, HVR residues and other residues in the variable domain (e.g., FR residues) are numbered herein according to Rabat et al. supra.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice, hamster and rats). In certain embodiments, the individual or subject is a human.

The term "monoclonal antibody" denotes an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be constructed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "non-naturally occurring amino acid residue" denotes an amino acid residue, other than the naturally occurring amino acid residues as listed above, which can be covalently bound to the adjacent amino acid residues in a polypeptide chain. Examples of non-naturally occurring amino acid residues are norleucine, ornithine, norvaline, homoserine. Further examples are listed in Ellman, et al., Meth. Enzym. 202 (1991) 301-336. Exemplary method for the synthesis of non-naturally occurring amino acid residues are reported in, e.g., Noren, et al., Science 244 (1989) 182 and Ellman et al., supra.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "positive linear pH gradient" denotes a pH gradient starting at a low more acidic) pH value and ending at a higher (i.e. less acidic, neutral or alkaline) pH value. In one embodiment the positive linear pH gradient starts at a pH value of about 5.5 and ends at a pH value of about 8.8.

The term "negative linear pH gradient" denotes a pH gradient starting at a high (i.e. neutral or alkaline) pH value and ending at a lower (i.e. neutral or acidic) pH value. In one embodiment the negative linear pH gradient starts at a pH value of about 7.4 and ends at a pH value of about 6.0.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J., et al., Kuby Immunology, 6th ed., W. H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The terms "variant", "modified antibody", and "modified fusion polypeptide" denotes molecules which have an amino acid sequence that differs from the amino acid sequence of a parent molecule. Typically such molecules have one or more alterations, insertions, or deletions. In one embodiment the modified antibody or the modified fusion polypeptide comprises an amino acid sequence comprising at least a portion of an Fc-region which is not naturally occurring. Such molecules have less than 100% sequence identity with the parent antibody or parent fusion polypeptide. In one embodiment the variant antibody or the variant fusion polypeptide has an amino acid sequence that has from about 75% to less than 100% amino acid sequence identity with the amino acid sequence of the parent antibody or parent fusion polypeptide, especially from about 80% to less than 100%, especially from about 85% to less than 100%, especially from about 90% to less than 100%, and especially from about 95% to less than 100%. In one embodiment the parent antibody or the parent fusion polypeptide and the variant antibody or the variant fusion polypeptide differ by one (a single), two or three amino acid residue(s).

II. Compositions and Methods

The human neonatal Fc receptor (FcRn) plays an important role in IgG catabolism. An IgGs in vitro FcRn binding properties/characteristics are indicative of its in vivo pharmacokinetic properties. Such in vitro methods would be of great value during antibody development as repeated in vivo studies can be avoided (reduced animal experiments, time and costs). Up to now, such analyses generally have been performed using plasmon surface resonance (SPR) assays (Wang, W., et al, Drug Metab. Disp. 39 (2011) 1469-1477; Datta-Mannan, A., et al., Drug Metab. Disp. 40 (2012)/ 1545-1555; Vaughn, D. E. and Bjorkman, P. J., Biochemistry 36 (1997) 9374-9380; Raghavan, M., et al., Proc. Natl. Acad. Sci. USA 92 (1995) 11200-11204; Martin, W. L. and Bjorkman, P. J., Biochemistry 38 (1999) 12639-12647). Calorimetric and asymmetrical flow field flow fractionation methods have also been described for assessing IgG binding affinity to FcRn (Huber, A. H., et al., J. Mol. Biol. 230 (1993) 1077-1083; Pollastrini, J., et al., Anal. Biochem 414 (2011) 88-98). In addition of being complex assays, several studies investigating the correlation between in vitro FcRn binding parameters determined by SPR and the serum half-life of antibodies in vivo failed so far to demonstrate such correlation despite improved binding reaction conditions and appropriate modeling (Gurbaxani, B., et al., Mol. Immunol. 43 (2006) 1462-1473; Gurbaxani, B. M. and Morrison, S. L., Mol. Immunol. 43 (2006) 1379-1389; Gurbaxani, B., Clin. Immunol. 122 (2007) 121-124). Engineering of the Fc-region of IgG1 to improve affinity of IgG1 to FcRn at pH 6 and at neutral pH as measured by SPR technology did not result in improved pharmacokinetics in cynomolgus monkeys (Yeung, Y. A., et al., J. Immunol. 182 (2009) 7663-7671). However, only modest increases in pH 6 FcRn affinity in the N434A IgG1 variant without concomitant significant binding to FcRn at pH 7.4 resulted in improved pharmacokinetics in primates demonstrating the importance of the FcRn release at pH 7.4 (see Yeung, Y. A., above).

A combination of known methods could achieve analytical results comparable to those of the FcRn affinity chromatography but at the expense of increased complexity and efforts.

Current standard methods do not appropriately reflect the physiologic pH dependency of the FcRn binding characteristics requiring acidic pH for endosomal binding, but neutral pH for IgG release at the cell surface. The pH milieu has influence on the self-association properties of the FcRn molecule. Current methods work under standard conditions at one given pH and, thus, detect just a snapshot of the complex FcRn-IgG interaction preventing a robust kinetic evaluation of the IgG-FcRn interaction. This also may be one of the reasons for the lacking correlation of FcRn affinity between in vitro FcRn analysis and in vivo pharmacokinetics found in several studies (see above).

SPR analysis of the IgG-FcRn interaction provides a qualitative result indicating expected or aberrant binding properties of a sample but does neither give a hint for the cause of aberrant binding nor a quantitative estimation of the amount of antibody with aberrant binding. Mass spectrometry also does just give qualitative information of a disturbed integrity of the IgG molecule. In contrast, the FcRn affinity chromatography allows to analyze the sample under appropriate physiologic conditions with a predominant 2:1 stoichiometry in a mixture of stoichiometries including 1:2, 1:1 and 2:2 stoichiometries and a pH gradient which can be adjusted to fine tune the separation of the different peaks found in a sample. The different peaks can be quantitated by their respective area under the curve and the eluate corresponding to each peak is amenable to secondary analysis for e.g. functionality determinations, re-chromatography or mass spectrometric analysis.

Additionally, in order to provide therapeutic regimens to treat the diversity of diseases know today and also those that will be revealed in the future a need for tailor made antibodies as well as Fc-part containing polypeptides exists.

To tailor made the FcRn binding characteristics of an antibody or an Fc-part containing fusion polypeptide the residues involved in Fc-part mediated effector functions are modified and the resulting modified antibodies and fusion polypeptides have to be tested. If the required characteristics are not met the same process is performed again.

In one embodiment the Fc-part is the fraction of an Fc-region that mediates the binding to the FcRn.

Thus, it would be advantageous to provide a method that predicts the changes in the characteristic properties of a modified antibody based on a simple chromatographical method and which does not require in vivo studies to analyze the changes of the characteristics in the modified antibody.

In some cases antibodies with extended half-life are desired. For example, drugs with an extended half-life in the circulation of a patient in need of a treatment require decreased dosing or increased dosing intervals. Such antibodies also have the advantage of increased exposure to a disease site, e.g. a tumor.

One aspect as reported herein is the use of an immobilized non-covalent complex of a neonatal Fc receptor (FcRn) and beta-2-microglobulin as affinity chromatography ligand.

It has been found that an affinity chromatography column comprising an immobilized non-covalent complex of a neonatal Fc receptor (FcRn) and beta-2-microglobulin as affinity chromatography ligand has an unexpected stability. It can be used for at least more than 100 chromatography cycles and up to about 200 chromatography cycles (equilibration separation regeneration) without a loss in performance (selectivity and/or binding capacity).

Also reported is an affinity chromatography column that comprises a matrix and matrix bound chromatographical functional groups, characterized in that the matrix hound chromatographical functional group comprises a non-covalent complex of neonatal Fc receptor (FcRn) and beta-2-microglobulin.

One aspect as reported herein is the use of a chromatography material comprising a non-covalent complex of neonatal Fc receptor (FcRn) and beta-2-microglobulin as ligand for the determination of the in vivo half-live of an antibody by determining the ratio of the retention times of the antibody and a reference antibody. In one embodiment the reference antibody is a full length human IgG1 antibody.

Herein is also reported a method for determining the in vivo half-live of an antibody in relation to a reference antibody by determining the ratio of the retention times determined on an FcRn affinity column as reported herein of the antibody and the reference antibody.

One aspect as reported herein is the use of a chromatography material comprising a non-covalent complex of neonatal Fc receptor (FcRn) and beta-2-microglobulin as ligand for the separating of antibodies or fusion polypeptides comprising at least an Fc-part.

Herein is also reported a method for separating antibodies or fusion polypeptides comprising at least an Fc-part.

In one embodiment the separating is selected from purifying, producing and analyzing.

One aspect as reported herein is the use of a chromatography material comprising a non-covalent complex of neonatal Fc receptor (FcRn) and beta-2-microglobulin as ligand for the separation of antibodies of the IgG1 subclass from antibodies of the IgG3 subclass.

One aspect as reported herein is the use of a chromatography material comprising a non-covalent complex of neonatal Fc receptor (FcRn) and beta-2-microglobulin as ligand for determining methionine oxidation of an antibody.

Herein is reported a method for determining the impact on FcRn binding oxidized methionine residues in the Fc-part of an antibody using an affinity chromatography method as reported herein.

One aspect as reported herein is the use of a chromatography material comprising a non-covalent complex of neonatal Fc receptor (FcRn) and beta-2-microglobulin as ligand for determining the oligomerization level of an antibody.

Herein is reported a method to determine the oligomerization level of an antibody using an affinity chromatography method as reported herein.

Generally, starting point for the method as reported herein is a parent antibody or a parent fusion polypeptide that is characterized by binding to the FcRn.

One aspect as reported herein is the use of a chromatography material comprising a non-covalent complex of neonatal Fc receptor (FcRn) and beta-2-microglobulin as ligand for screening a library of modified antibodies or modified fusion polypeptides of a parent antibody or a parent fusion polypeptide which comprise at least an FcRn binding portion of an Fc-region for those modified antibodies or modified fusion polypeptides that have an altered binding affinity for FcRn compared to the parent antibody or parent fusion polypeptide.

Herein is reported a method for screening a library of modified antibodies or modified fusion polypeptides of a parent antibody or a parent fusion polypeptide which comprise at least an FcRn binding portion of an Fc-region for those modified antibodies or modified fusion polypeptides that have an altered binding affinity for FcRn compared to the parent antibody or parent fusion polypeptide, the method comprising the following steps:
  (a) applying the individual members of the library and the parent antibody or parent fusion polypeptide to an FcRn affinity chromatography column as reported herein;
  (b) recovering the individual members of the library with a pH gradient and determining the individual retention times; and
  (c) selecting those antibodies or fusion polypeptides that have altered binding affinity for Ran compared to the parent antibody or parent fusion polypeptide.

Herein is reported a method for purifying an antibody or a fusion polypeptide, which comprises at least an FcRn-binding part of an Fc-region, from a mixture of polypeptides, the method comprising applying the mixture to a FcRn affinity column as reported herein and eluting the antibodies or the fusion polypeptide, which comprises at least an FcRn binding portion of an Fc-region, with a pH gradient and thereby purifying the antibody or the fusion polypeptide. In one embodiment the FcRn-part of an Fc-region is of a human. Fc-region, or a mouse Fc-region, or a cynomolgus Fc-region, or a rabbit Fc-region, or a hamster Fc-region.

The terms "a" and "an" denote one or two or three or four or five or six and up to $10^9$.

In one embodiment, the reaction/production mixture or the crude or partly purified cultivation supernatant is applied to the FcRn affinity column at a first pH value and the antibody or the fusion polypeptide is recovered from the FcRn affinity column at a second pH value.

In one embodiment the first pH value is about pH 3.5 to about pH 7.5, In one embodiment the first pH value is about pH 4 to about pH 7. In one embodiment the first pH value is about pH 4.5 to about pH 6.5. In one embodiment the first pH value is about pH 5 to about pH 6. In one embodiment the first pH value is about pH 5 or about pH 5.5 or about pH 6.

In one embodiment the first pH value is selected from about pH 3.5, about pH 3.6, about pH 3.7, about pH 3.8, about pH 3.9, about pH 4.0, about pH 4.1, about pH 4.2, about pH 4.3, about pH 4.4, about pH 4.5, about pH 4.6, about pH 4.7, about pH 4.8, about pH 4.9, about pH 5.0, about pH 5.1, about pH 5.2, about pH 5.3, about pH 5.4, about pH 5.5, about pH 5.6, about pH 5.7, about pH 5.8, about pH 5.9, about pH 6.0, about pH 6.1, about pH 6.2, about pH 6.3, about pH 6.4, about pH 6.5, about pH 6.6, about pH 6.7, about pH 6.8, about pH 6.9, about pH 7.0, about pH 7.1, about pH 7.2, about pH 7.3, about pH 7.4, and about pH 7.5.

In one embodiment the second pH value is about pH 8 to about pH 9.5. In one embodiment the second pH value is about pH 8.5 to about pH 9. In one embodiment the second pH value is about pH 8.8.

In one embodiment the second pH value is selected from about pH 8.0, about pH 8.1, about pH 8.2, about pH 8.3, about pH 8.4, about pH 8.5, about pH 8.6, about pH 8.7, about pH 8.8, about pH 8.9, about pH 9.0, about pH 9.1, about pH 9.2, about pH 9.3, about pH 9.4, and about pH 9.5.

In one embodiment each of the given first pH values of about pH 3.5, about pH 3.6, about pH 3.7, about pH 3.8, about pH 3.9, about pH 4.0, about pH 4.1, about pH 4.2, about pH 4.3, about pH 4.4, about pH 4.5, about pH 4.6, about pH 4.7, about pH 4.8, about pH 4.9, about pH 5.0, about pH 5.1, about pH 5.2, about pH 5.3, about pH 5.4, about pH 5.5, about pH 5.6, about pH 5.7, about pH 5.8, about pH 5.9, about pH 6.0, about pH 6.1, about pH 6.2, about pH 6.3, about pH 6.4, about pH 6.5, about pH 6.6, about pH 6.7, about pH 6.8, about pH 6.9, about pH 7.0, about pH 7.1, about pH 7.2, about pH 7.3, about pH 7.4, and about pH 7.5 is combined with each of the given second pH values of about pH 8.0, about pH 8.1, about pH 8.2, about pH 8.3, about pH 8.4, about pH 8.5, about pH 8.6, about pH 8.7, about pH 8.8, about pH 8.9, about pH 9.0, about pH 9.1, about pH 9.2, about pH 9.3, about pH 9.4, and about pH 9.5.

One aspect as reported herein is the use of a chromatography material comprising a non-covalent complex of neonatal Fc receptor (FcRn) and beta-2-microglobulin as ligand for identifying antibodies or fusion polypeptides that comprise at least an FcRn-binding portion of an Fc-region (e.g., a constant domain of an immunoglobulin such as IgG1) which exhibit altered binding to the neonatal Fc receptor (FcRn).

Herein is provided a method for identifying antibodies or fusion polypeptides that comprise at least an FcRn-binding portion of an Fc-region (e.g., a constant domain of an immunoglobulin such as IgG1) which exhibit altered binding to the neonatal Fc receptor (FcRn).

Such modified antibodies or fusion polypeptides show either increased or decreased binding to FcRn when compared to a parent antibody or fusion polypeptide or compared to a reference antibody or reference fusion protein, and, thus, have an increased or decreased half-life in serum, respectively.

Fc-region variants with increased affinity for the FcRn (i.e. increased retention time on an FcRn column but still eluting before a pH value of pH 7.4 as reported herein compared to a parent antibody or reference antibody) are predicted to have longer serum half-lives compared to those with decreased affinity for the FcRn, Fc-region variants with increased affinity for the FcRn have applications in methods of treating mammals, especially humans, where long half-life of the administered antibody or fusion polypeptide is desired, such as in the treatment of a chronic disease or disorder. Fc-region variants with decreased affinity for the FcRn have applications in methods of treating mammals, especially humans, where a short half-life of the administered antibody or fusion polypeptide is desired, such as an vivo diagnostic imaging.

It is very likely that Fc-region variants with decreased FcRn binding affinity will be able to cross the placenta and, thus, can be used in the treatment of diseases or disorders in pregnant women especially of unborn children. In addition, reduced FcRn binding affinity may be desired for those drugs intended for application/transport to the brain, kidney, and/or liver.

One aspect as reported herein is the use of a chromatography material comprising a non-covalent complex of neonatal Fc receptor (FcRn) and beta-2-microglobulin as ligand for identifying antibodies or fusion polypeptides that exhibit reduced transport across the epithelium of kidney glomeruli from the vasculature.

In one embodiment the antibody or fusion polypeptide comprising a modified Fc-region as reported herein exhibit reduced transport across the epithelium of kidney glomeruli from the vasculature.

One aspect as reported herein is the use of a chromatography material comprising a non-covalent complex of neonatal Fc receptor (FcRn) and beta-2-microglobulin as ligand for identifying antibodies or fusion polypeptides that exhibit reduced transport across the blood brain barrier from the brain into the vascular space.

In one embodiment the antibody or fusion polypeptide comprising a modified Fc-region of human origin as reported herein exhibit reduced transport across the blood brain barrier (BBB) from the brain into the vascular space.

Herein are reported methods of making such modified antibodies and fusion polypeptides comprising at least an FcRn binding pardon of an Fc-region and methods of using such modified antibodies and fusion polypeptides.

In one embodiment the antibody or the fusion polypeptide as reported herein comprises at least one binding site (e.g. at least one antigen binding site, or at least one receptor binding site, or at least one ligand binding site). In one embodiment, the antibody or fusion polypeptide as reported herein comprises at least two binding sites (e.g. at least two antigen binding sites, or at least two receptor binding sites, or at least two ligand binding sites, or at least one antigen binding site and at least one receptor binding site, or at least one antigen binding site and at least one ligand binding site, or at least one receptor binding site and at least one ligand binding site). In one embodiment the antibody or the fusion polypeptide as reported herein comprises three binding sites (e.g. at least three antigen binding sites, or at least three receptor binding sites, or at least three ligand binding sites, or any mixture of at least three binding sites of the before). In one embodiment the antibody or the fusion polypeptides as reported herein comprise four binding sites.

In one embodiment of all aspects as reported herein is the at least a part of an Fc-region at least a part of an Fc-region of human origin. In one embodiment of all aspects as reported herein is the FcRn selected from human FcRn, cynomolgus FcRn, mouse FcRn, rat FcRn, sheep FcRn, dog FcRn and rabbit FcRn.

In one embodiment of all aspects as reported herein the beta-2-microglobulin is from the same species as the FcRn.

In one embodiment of all aspects as reported herein the beta-2-microglobulin is from a different species as the FcRn.

In one embodiment the Fc-regions or the FcRn binding parts of an Fc-region are derived from heavy chains of any isotype.

In one embodiment the at least a part of an Fc-region comprises at least amino acid residues 282-340 of a CH2 domain of human origin (SEQ ID NO: 01, numbering according to Kabat). In one embodiment the at least a portion of an Fc-region comprises a complete CH2 domain (about amino acid residues 231-340 of an antibody heavy chain polypeptide Fc-region of human origin according to EU numbering according to Kabat). In one embodiment the at least a portion of an Fc region comprises at least a CH2 domain, and at least one of a hinge region (about amino acid residues 216-230 of an antibody heavy chain polypeptide Fc-region of human origin according to EU numbering) or a CH3 domain (about amino acid residues 341-446 of an antibody heavy chain polypeptide Fc-region of human origin according to EU numbering). In one embodiment the at least a portion of an Fc-region comprises a CH2 and a CH3 domain of an antibody heavy chain of human origin. In one embodiment the at least a portion of an Fc-region comprises a hinge, a CH2 domain, and CH3 domain of an antibody heavy chain. Fc-region of human origin, Fc-regions of human origin or FcRn binding parts of an Fc-region of human origin portions may be derived from heavy chains of any isotype, such as IgG1 (SEQ ID NO: 03), IgG2 (SEQ ID NO: 04), IgG3 (SEQ ID NO: 05), and IgG4 (SEQ ID NO: 06). In one embodiment the human isotype is IgG1.

The Fc-region of the parent antibody or comprised in the parent fusion polypeptide can be derived from different immunoglobulin molecules and/or different immunoglobulin isotypes. For example, a parent antibody or a parent fusion polypeptide may comprise a CH2 domain derived from an IgG1 isotype immunoglobulin and a hinge region derived from an IgG3 isotype immunoglobulin. Also for example, a parent antibody or a parent fusion polypeptide can comprise a hinge region derived, in part, from the IgG1 immunoglobulin subtype and, in part, from the IgG3 immunoglobulin subtype as long as these are of human origin. For example, a parent antibody or a parent fusion polypeptide can comprise a chimeric hinge region derived, in part, from an IgG1 immunoglobulin isotype and, in part, from an IgG4 immunoglobulin isotype.

The parent antibody or the parent fusion polypeptide as reported herein comprise at least one Fc-region or one FcRn-binding part thereof. In one embodiment the parent antibody or parent polypeptide additionally comprises at least one binding domain (in one embodiment selected from an antigen binding domain, a receptor binding domain, or a ligand binding domain). In one embodiment the parent antibody or parent fusion polypeptides comprise at least one binding domain and at least one Fc-region or one FcRn binding part thereof. In one embodiment the parent antibody or parent fusion polypeptide comprises two binding domains and two Fc-regions or two FcRn-binding parts thereof.

In one embodiment the parent antibody or the parent fusion polypeptide as reported herein comprise at least one binding domain that specifically binds to a target which mediates a biological effect (in one embodiment a ligand capable of binding to a cell surface receptor or a cell surface receptor capable of binding a ligand) and mediates transmission of a negative or positive signal to a cell together with at least one Fc-region or FcRn binding part thereof. In one embodiment the mediation of the biological effect is at a pH value of about pH 7.4. In one embodiment the parent antibody or parent fusion polypeptide comprises at least one binding domain specific for an antigen targeted for reduction or elimination (in one embodiment a cell surface antigen or a soluble antigen) and at least one Fc-region or one FcRn binding part thereof.

Antibodies specifically binding to a target can be raised in mammals by multiple subcutaneous or intraperitoneal injections of the relevant antigen (e.g. purified antigen, cells or cellular extracts comprising such antigens, or DNA encoding for such antigen) and optionally an adjuvant.

In one embodiment the antibody is a monoclonal antibody.

In one embodiment the fission polypeptide as reported herein comprises an antibody fragment (e.g. a scFv molecule, a minibody, a tetravalent minibody, or a diabody) operably linked to an FcRn binding portion. In one embodiment, the FcRn binding portion is a complete antibody heavy chain Fc-region.

In one embodiment the parent antibody is a bispecific antibody or the parent fusion polypeptide comprises a bispecific antibody or a bispecific antibody fragment.

In one embodiment the parent antibody is a chimeric antibody.

In one embodiment the parent fusion polypeptide comprises at least an FcRn-binding part of an Fc-region. In one embodiment the parent fusion polypeptide as reported herein comprise one or more binding domain(s) which in turn each comprise one binding site. The parent fusion polypeptide can be bispecific (with one binding site specifically binding to a first target and a second binding site specifically binding to a second target) or multivalent (with two binding sites specifically binding to the same target).

In one embodiment of all previous aspects the pH is a gradient from about pH 5.5 to about pH 8.8.

In one embodiment the pH is a gradient from about pH 5 to pH 6, or from about pH 6 to about pH 7, or from about pH 7 to about pH 8.

Generally, the binding domain is fused to the C-terminus or the N-terminus of the at least an FcRn binding portion of an Fc-region.

One aspect as reported herein is the use of a chromatography material comprising a non-covalent complex of neonatal Fc receptor (FcRn) and beta-2-microglobulin as ligand for selecting antibodies with a binding to the FcRn at a pH value of pH 7.4 for in vivo (co-)targeting, in one embodiment the co-targeting is internalization.

Thus, in one embodiment the first pH is about pH 7.4. In one embodiment the second pH is about pH 6.0.

In general the soluble extracellular domain of FcRn (SEQ ID NO: 07 for human FcRn) with C-terminal His-Avi Tag (SEQ ID NO: 08) was co-expressed with $\beta_2$-microglobulin (SEQ ID NO: 09 for human beta-2-microglobulin) in mammalian cells. The non-covalent FcRn-microglobulin complex was biotinylated and loaded onto streptavidin derivatized sepharose.

In one embodiment of all aspects as reported herein the non-covalent complex of neonatal Fc receptor (FcRn) and beta-2-microglobulin is bound to a solid phase.

A "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microliter plates; solid strips; and cuvettes, tubes or other spectrometer sample containers. A solid phase component of an assay is distinguished from inert solid surfaces in that a "solid support" contains at least one moiety on its surface, which is intended to interact chemically with a molecule. A solid phase may be a stationary component, such as a chip, tube, strip, cuvette, or microtiter plate, or may be non-stationary components, such as beads and microparticles. Microparticles can also be used as a solid support for homogeneous assay formats. A variety of microparticles that allow both non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, May 1 (1998) 322A-327A, which is incorporated herein by reference. In one embodiment the solid support is sepharose.

In one embodiment the conjugation of the non-covalent complex to the solid phase is performed by chemically binding via N-terminal and/or ε-amino groups (lysine), ε-amino groups of different lysins, carboxy-, sulfhydryl-, hydroxyl-, and/or phenolic functional groups of the amino acid backbone of the antibody, and/or sugar alcohol groups of the carbohydrate structure of the antibody.

In one embodiment the non-covalent complex is conjugated to the solid phase via a specific binding pair. In one embodiment the non-covalent complex is conjugated to biotin and immobilization to a solid support is performed via solid support immobilized avidin or streptavidin.

A specific binding pair (first component/second component) is in one embodiment selected from streptavidin or avidin/biotin, antibody/antigen (see, for example, Hermanson, (G. T., et al., Bioconjugate Techniques, Academic Press (1996)), lectin/polysaccharide, steroid/steroid binding protein, hormone/hormone receptor, enzyme/substrate, IgG/Protein A and/or G, etc.

The recovering of antibody bound to the FcRn affinity column as reported herein in the uses and methods as reported herein is by a linear gradient elution. In one embodiment the linear gradient is a pH gradient or a conductivity gradient.

In principle any buffer substance can be used in the methods as reported herein.

Fc residues critical to the mouse Fc-mouse FcRn interaction have been identified by site-directed mutagenesis (see e.g. Dall'Acqua, W. F., et al. J. Immunol. 169 (2002) 5171-5180). Residues I253, H310, H433, N434, and H435 (EU numbering according to Kabat) are involved in the interaction (Medesan, C., et al., Eur. J. Immunol. 26 (1996) 2533; Firan, M., et al., Int. Immunol. 13 (2001) 993; Kim, J. K., et al., Eur. J. Immunol. 24 (1991) 542). Residues I253, H310, and H435 were found to be critical for the interaction of human Fc with murine FcRn (Kim, J. K., et al., Eur. J. Immunol. 29 (1999) 2819). Residues M252Y, S254T, T256E have been described by Dall'Acqua et al. to improve FcRn binding by protein-protein interaction studies (Dall'Acqua, W. F., et at J. Biol. Chem. 281 (2006) 23514-23524). Studies of the human Fc-human FcRn complex have shown that residues I253, S254, H435, and Y436 are crucial for the interaction (Firan, M., et al., Int. Immunol. 13 (2001) 993; Shields, R. L., et al., J. Biol. Chem. 276 (2001) 6591-6604). In Yeung, Y. A., et al. (J. Immunol. 182 (2009) 7667-7671) various mutants of residues 248 to 259 and 301 to 317 and 376 to 382 and 424 to 437 have been reported and examined.

The retention time of different antibodies obtained with different elution buffers is shown in the following table.

TABLE

| elution buffer | anti-Her2 antibody (I253H-mutant) | anti-Ox40L antibody | anti-Abeta antibody (wild-type) | anti-Abeta antibody (YTE-mutant) peak 1 | peak2 |
|---|---|---|---|---|---|
| 20 mM Tris/HCl, with 150 mM NaCl, adjusted to pH 8.8 | no binding | 45 | 45.5 | 52.5 | 66 |
| 20 mM Tris/HCl, with 300 mM NaCl, adjusted to pH 8.8 | not determined | 42.5 | 43 | 48.5 | 51.5 |
| 20 mM Tris/HCl, with 50 mM NaCl, adjusted to pH 8.8 | not determined | 43 | 44 | 51 | — |
| 20 mM HEPES, with 150 mM NaCl, adjusted to pH 8.6 | not determined | 48 | 48.5 | 63 | 76 |

The term YTE-mutant denotes the triple mutant M252Y/S254T/T256E.

In one embodiment a pharmaceutically acceptable buffer substance is used, such as e.g. phosphoric acid or salts thereof, acetic acid or salts thereof, citric acid or salts thereof; morpholine, 2-(N-morpholino) ethanesulfonic acid (MES) or salts thereof, histidine or salts thereof, glycine or salts thereof, tris (hydroxymethyl) aminomethane (TRIS) or salts thereof, (4-(2-hydroxyethyl-1-piperazineethanesulfonic acid (HEPES) or salts thereof.

In one embodiment the buffer substance is selected from phosphoric acid or salts thereof; or acetic acid or salts thereof; or citric acid or salts thereof; or histidine or salts thereof.

In one embodiment the buffer substance has a concentration of from 10 mM to 500 mM. In one embodiment the buffer substance has a concentration of from 10 mM to 300 mM. In one embodiment the buffer substance has a concentration of from 10 mM to 250 mM. In one embodiment the buffer substance has a concentration of from 10 mM to 100 mM. In one embodiment the buffer substance has a concentration of from 15 mM to 50 mM. In one embodiment the buffer substance has a concentration of about 20 mM.

In one embodiment the buffer substance in the first solution and the buffer substance in the second solution are the same buffer substance.

In one embodiment the buffer substance in the first solution and the buffer substance in the second solution are different buffer substances.

In one embodiment the first solution has a pH value of about pH 3.5 to about pH 7.5. In one embodiment the first solution has a pH value of about pH 5 to about pH 6. In one embodiment the first solution has a pH value of about pH 5.5.

In one embodiment the second solution has a pH value of about pH 7.0 to about pH 9.5. In one embodiment the second solution has a pH value of about pH 8 to about pH 9. In one embodiment the second solution has a pH value of about pH 8.2 to about pH 8.8.

An exemplary first solution comprises 20 mM MES and 150 mM NaCl, adjusted to pH 5.5.

An exemplary second solution comprises 20 mM TRIS and 150 mM NaCl, adjusted to pH 8.8

An exemplary second solution comprises 20 mM HEPES adjusted to pH 8.6.

An exemplary second solution comprises 20 mM TRIS adjusted to pH 8.2.

In one embodiment the buffered solution comprises an additional salt. In one embodiment the additional salt is selected from sodium chloride, sodium sulphate, potassium chloride, potassium sulfate, sodium citrate, or potassium citrate. In one embodiment comprises the buffered solution of from 50 mM to 1000 mM of the additional salt. In one embodiment comprises the buffered solution of from 50 mM to 750 mM of the additional salt. In one embodiment comprises the buffered solution of from 50 mM to 500 mM of the additional salt. In one embodiment comprises the buffered solution of from 50 mM to 750 mM of the additional salt. In one embodiment comprises the buffered solution about 50 mM to about 300 mM of the additional salt.

In one embodiment the first and/or second solution comprises sodium chloride. In one embodiment the first and/or second solution comprises of about 50 mM to about 300 mM sodium chloride.

It has been found that the kind of salt and buffer substance influences the retention time and the resolution. An optimal salt concentration for binding of antibodies to FcRn can be determined (150 mM NaCl). If the salt concentration is higher (300 mM) binding to FcRn is reduced/a shorter retention time is obtained. Same is true for lower salt concentration (50 mM HEPES pH 8.6 prolonged retention time for all tested antibodies.

As can be seen from FIG. 1 the amount of applied antibody shows a linear correlation to the area under the curve of the eluted peak.

Eight antibodies were analyzed as complete antibody and after cleavage with the enzyme IDES. The cleavage was controlled by SDS page and analytical SEC. Fc part and Fab part of the antibody were separated by preparative SEC. In the following Table the retention times of the complete antibody, of the Fab part and of the Fc part is given.

TABLE

| antibody | complete antibody | Fc part | Fab part |
|---|---|---|---|
| anti-Her2 antibody (I253H mutant) | no binding | not determined | not determined |
| anti-IGF-1R antibody | 44.5 | 45 | no binding |
| anti-IL13Rα antibody | 44.5 | 45 | no bidning |
| anti-Her2 antibody | 45 | 45 | no binding |
| anti-IL 6R antibody | 45 | 45 | no binding |
| anti-Ox40L antibody | 45 | 45 | no binding |
| anti-Abeta antibody (wild-type) | 45 | 45 | no binding |
| anti-Abeta antibody (YTE mutant) | peak 1: 52.5 peak 2: 66 | 52 | no binding |

The term YTE-mutant denotes the triple mutant M25Y/S254T/T256E.

In general the retention time of antibodies having a wild-type Fc part (IgG1 or IgG2 or IgG4) varies between 45 and 49 min (tested with 35 therapeutic antibodies against 36 antigens, data not shown).

In the following table the retention time with respect to amount of immobilized FcRn receptor per gram of column material is shown.

| elution buffer: | retention time [min] | | | | |
|---|---|---|---|---|---|
| 20 mM Tris/HCl, with 150 mM NaCl, adjusted to pH 8.8 | anti-Her2 antibody (I253H-mutant) | anti-Ox40L antibody | anti-Abeta antibody (wild-type) | anti-Abeta antibody (YTE-mutant) peak 1 | peak2 |
| 1.2 mg FcRn/g solid phase | not determined | 42.5 | 42.5 | 48.5 | 54 |
| 3 mg FcRn/g solid phase | no binding | 45 | 45.5 | 52.5 | 66 |
| 6 mg FcRn/g solid phase | not determined | 48.5 | 49 | 53 | 74 |
| 12 mg FcRn/g solid phase | not determined | 48.5 | 49 | 58 | 75 |

The term YTE-mutant denotes the triple mutant M252Y/S254T/T256E.

The anti-Abeta antibody FAB-fragment comprises a glycosylation site.

Thus, one aspect as reported herein is the use of a chromatography material comprising a non-covalent complex of neonatal Fc receptor (FcRn) and beta-2-microglobulin as ligand for detecting FAB modification. In one embodiment the modification is glycosylation, or charge distribution.

In general the retention time in the methods and uses as reported herein is depending on steepness of the pH gradient and the employed salt concentration. The wild-type antibody is used as reference and a weaker binding is indicated by a shorter retention time (=earlier elution) whereas a stronger binding is indicated by a longer retention time (=later elution), but still before a pH value of pH 7.4.

It has been found that different mutants of the Fc part of the IgG behave different on the FcRn column, displaying modified retention times.

For example the anti-Abeta antibody mutant YTE shows an increased retention time. The second peak of the anti-Abeta antibody YTE mutant is due to an additional glycosylation site introduced in the Fab part.

Figure 2:
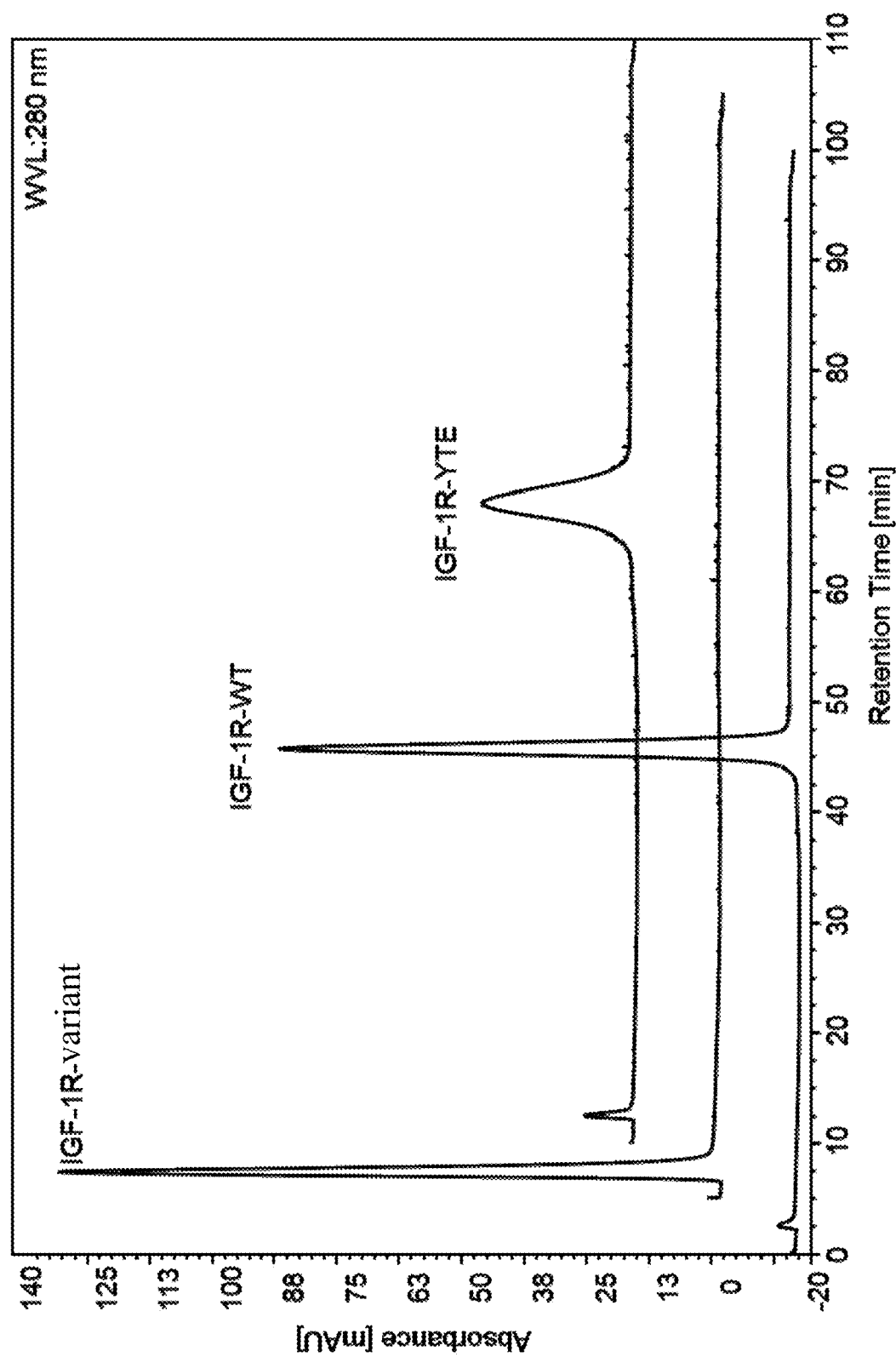
FIG. 2 Chromatogram of anti-IGF-1R antibody wild-type and YTE-mutant on FcRn column as reported herein.

For example the anti-IGF-1R antibody mutant YTE shows an increased retention time (see FIG. 2).

| antibody | retention time [min] |
|---|---|
| anti-IGF-1R antibody (wild-type) | 44.5 |
| anti-IGF-1R antibody (YTE-mutant) | 57.5 |
| anti-Abeta antibody (wild-type) | 45 |
| anti-Abeta antibody (YTE mutant) | peak 1: 52.5 peak 2: 66 |

The term YTE-mutant denotes the triple mutant M252Y/S254T/T256E.

It has been found that with the FcRn column as reported herein it is possible to identify FcRn binding relevant amino acids and to rank the mutants in comparison to the not modified wild-type antibody.

Aspects as reported herein is the use of a chromatography material comprising a non-covalent complex of neonatal Fc receptor (FcRn) and beta-2-microglobulin as ligand for identifying FcRn binding relevant amino acids and for ranking the mutants in comparison to the not modified wild-type antibody.

The results obtained with an anti-Her2 antibody are presented in the following table (see e.g. WO 2006/031370 as exemplary reference).

| mutation | retention time [min] | retention time [% of wild-type] |
|---|---|---|
| I253H | no binding | — |
| M252D | no binding | — |
| S254D | no binding | — |
| R255D | 41.4 | 89 |
| M252H | 43.6 | 94 |
| K288E | 45.2 | 98 |
| L309H | 45.5 | 98 |
| E258H | 45.6 | 99 |
| T256H | 46.0 | 99 |
| K290H | 46.2 | 100 |
| D98E | 46.2 | 100 |
| wild-type | 46.3 | 100 |
| K317H | 46.3 | 100 |
| Q311H | 46.3 | 100 |
| E430H | 46.4 | 100 |
| T307H | 47.0 | 102 |
| N434H | 52.0 | 112 |

It has been found that antibodies that showed a late elution from the FcRn column, i.e. that had a longer retention time on the FcRn column, had a longer half-life in vivo. The in vivo data is shown in the following table.

| antibody | retention time [min] | In vivo half-life [h] |
|---|---|---|
| anti-Abeta antibody (wild-type) | 45.5 | 103 +/− 51 |
| anti-Abeta antibody (YTE-mutation) | 52.5/66 | 197 +/− 53 |
| anti-IGF-1R antibody (wild-type) | 45.5 | 97 +/− 9 |
| anti-IGF-1R antibody (YTE-mutant) | 58 | 211 +/− 41 |

The term YTE-mutant denotes the triple mutant M252Y/S254T/T256E.

One aspects as reported herein is the use of a chromatography material comprising a non-covalent complex of neonatal Fc receptor (FcRn) and beta-2-microglobulin as ligand for determining the in vivo half-life of an antibody.

The set of in vitro and in vivo experiments conducted with wild-type IgG and IgG variants with YTE-mutations in the Fc part allowed to show a semi-quantitative correlation of the findings in the FcRn affinity chromatography with those of the in vivo pharmacokinetic studies with mice transgenic for human FcRn (Spiekerman, G. M., et al., J. Exp. Med, 196 (2002) 303-310; Dall'Acqua, W. F., et al., J. Biol. Chem, 281 (2006) 23514-23524). The YTE-mutation leads to a significantly prolonged half-life and slower plasma clearance. The longer in vivo half-life corresponded to a longer retention time in the FcRn chromatography. An extended half-life of an Fc-engineered trastuzumab variant recently was shown to have enhanced in vitro binding to FcRn as measured by flow cytometry (Petkova, S. B., et al., Int. Immunol. 18 (2006) 1759-1769). A variant of the anti-VEGF IgG1 antibody bevacizumab with 11-fold improved FcRn affinity was shown to have a five-fold extended half-life in human FcRn transgenic mice and a three-fold longer half-life in cynomolgus monkeys (Zalevsky, J., et al., Nat. Biotechnol. 2.8 (2010) 157-159).

Figure 3:
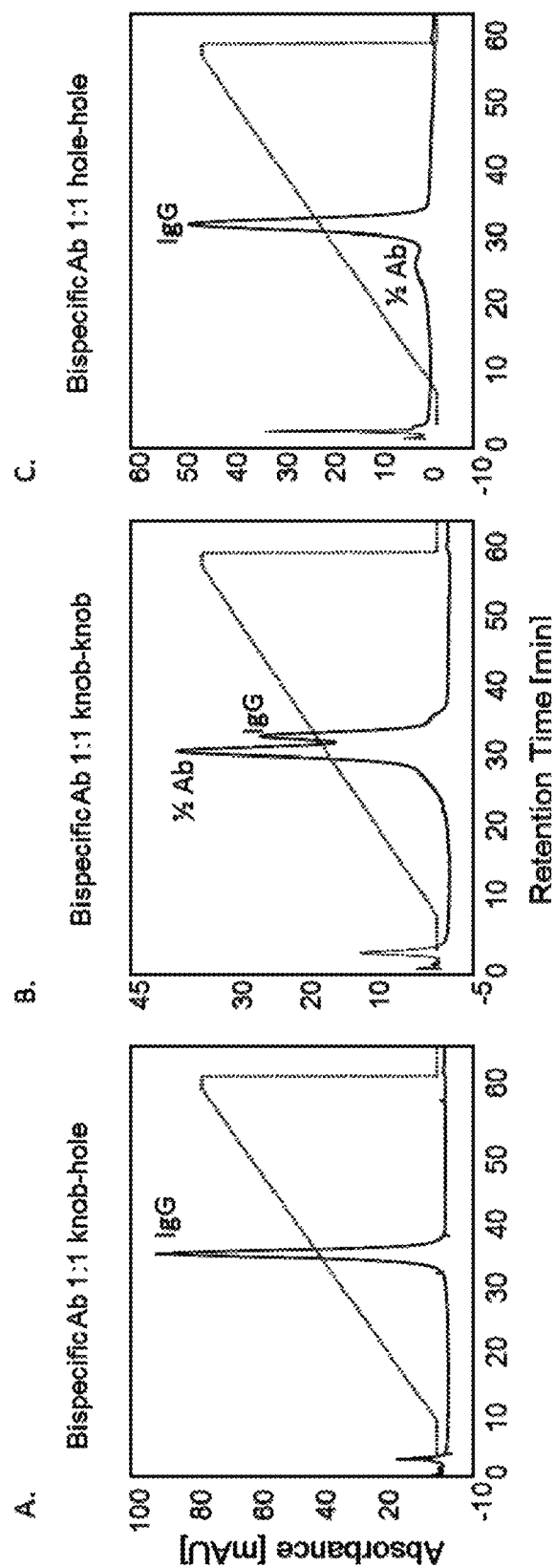
FIG. 3 FcRn chromatography (A/B/C top row) of different antibody preparations containing different amounts of half antibodies as can be seen in CE-SDS analysis (A/B/C bottom row).

It has been found that the analysis and removal of half antibodies in IgG preparations can be achieved by using an FcRn column as reported herein. An exemplary FcRn column chromatography is shown in FIG. 3.

One aspects as reported herein is the use of a chromatography material comprising a non-covalent complex of neonatal Fc receptor (FcRn) and beta-2-microglobulin as ligand for the removal of half antibodies from IgG preparations.

Figure 4:
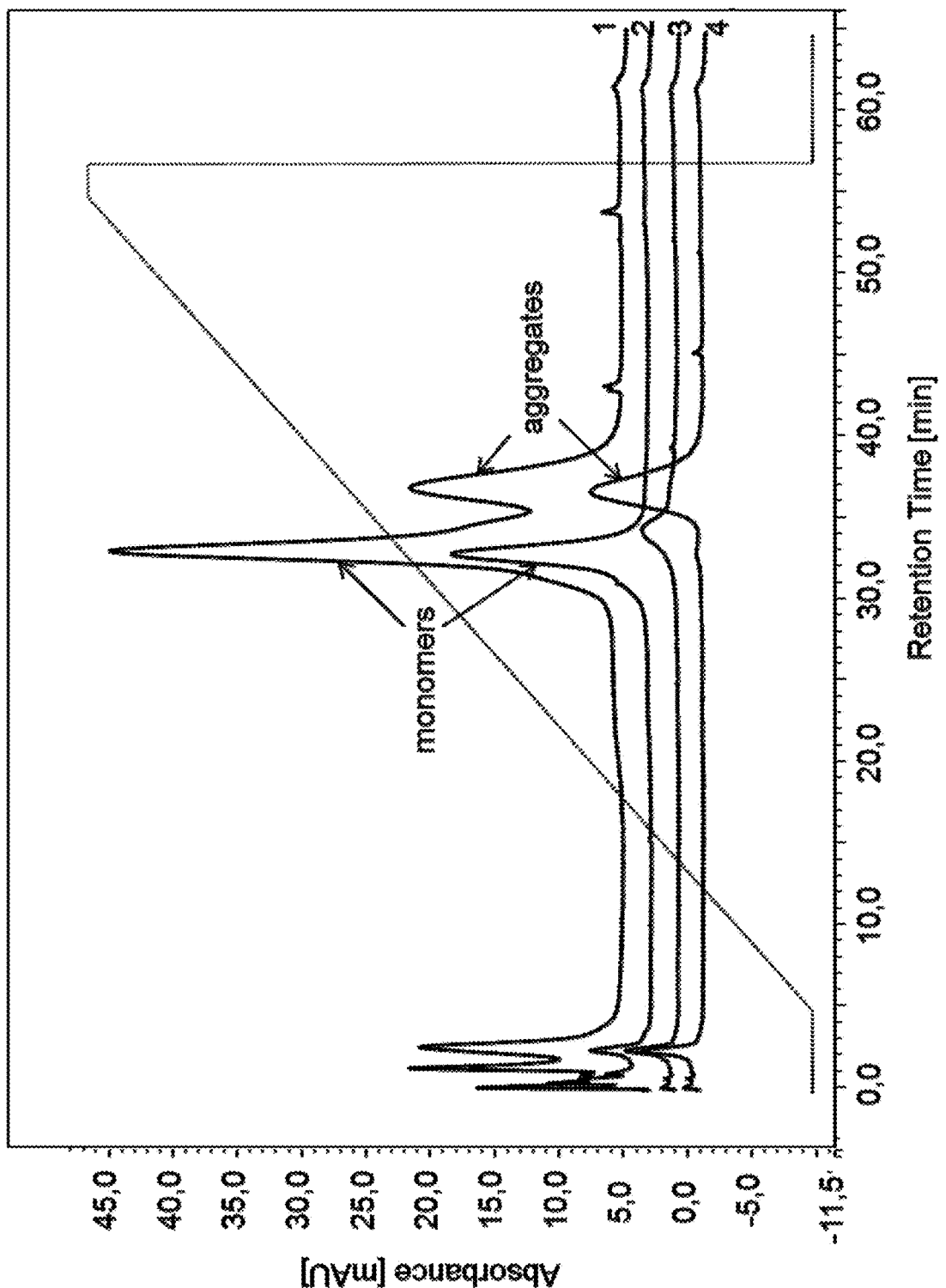
FIG. 4 FcRn chromatography of different antibody preparations containing different amounts of antibody monomer and aggregates.

It has been found that oligomers and aggregates can be separated by FcRn chromatography as reported herein (see FIG. 4).

One aspects as reported herein is the use of a chromatography material comprising a non-covalent complex of neonatal Fc receptor (FcRn) and beta-2-microglobulin as ligand for the removal of antibody aggregates and antibody oligomers from IgG preparations.

Figure 5:
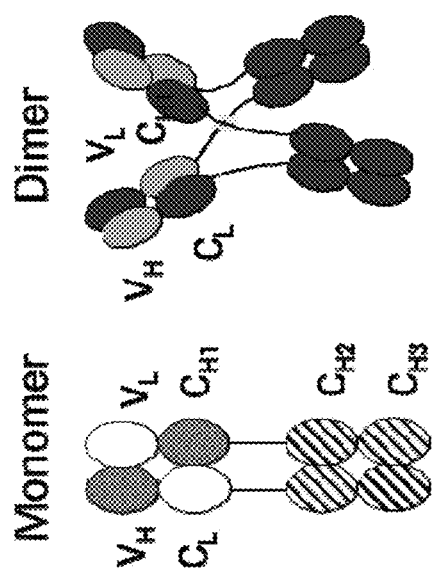
FIG. 5 Influence of the retention time in an FcRn chromatography by the number of Fc-regions in the chromatographed molecule.
Figure 5:
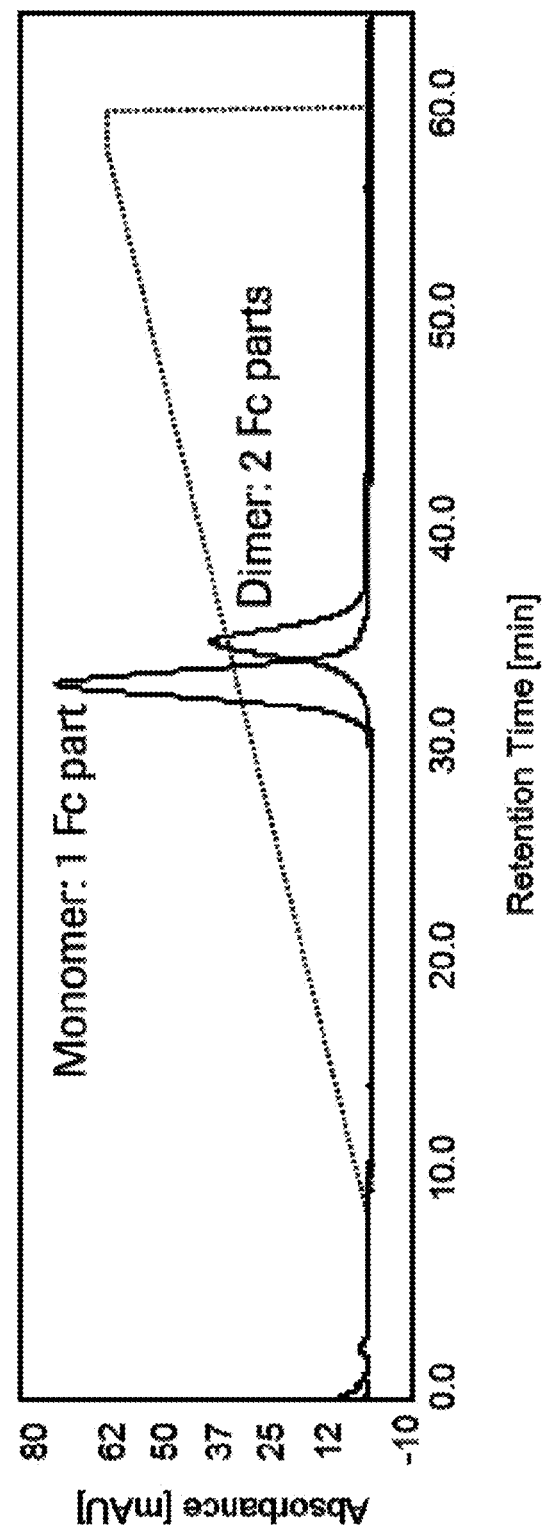

It has been found that the retention time is influenced by number of Fc parts comprised in the analyte molecule. This was shown by using constructs containing one or two Fc parts (see FIG. 5).

Figure 6:
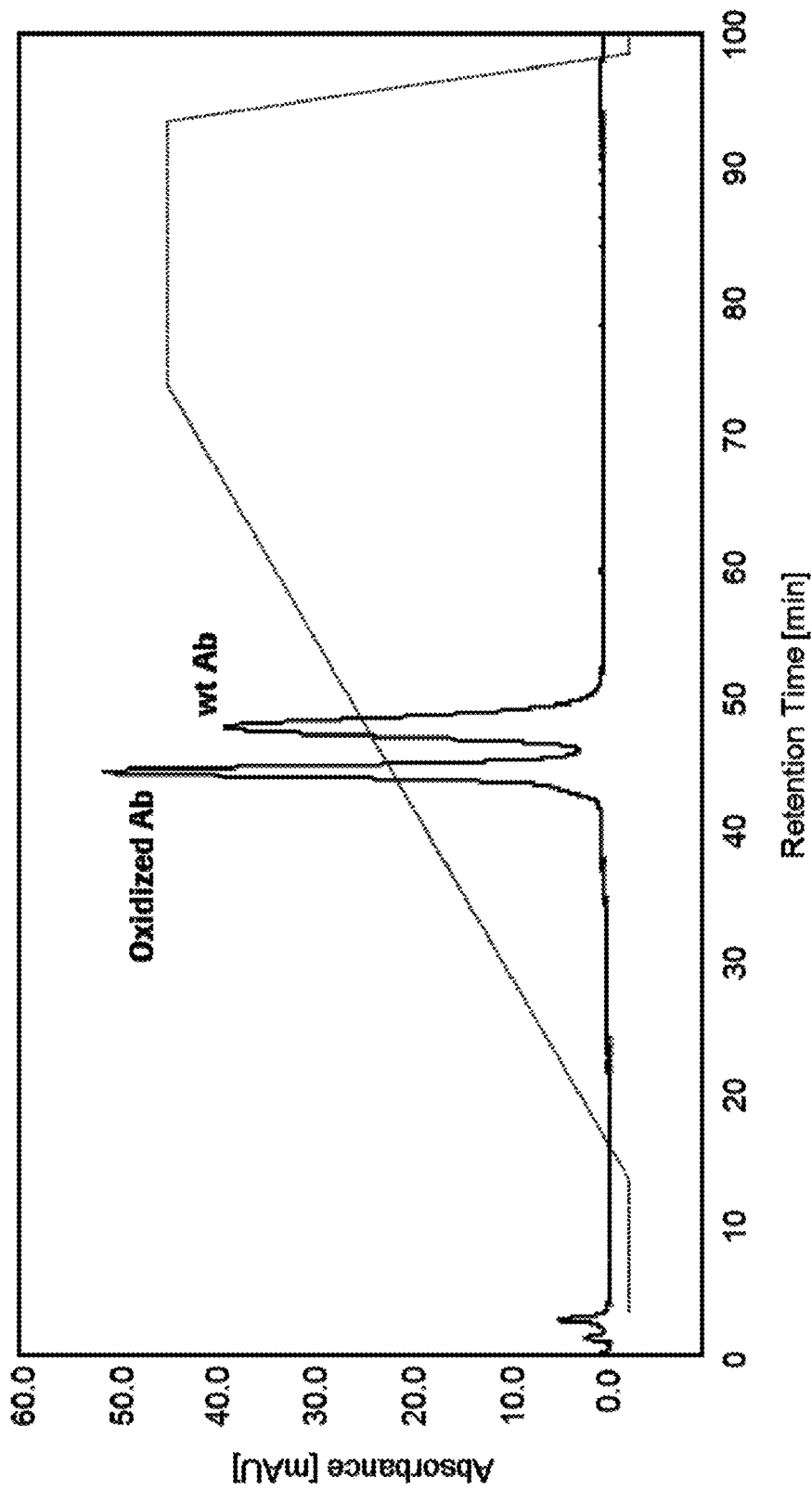
FIG. 6 impact on oxidation of an antibody on FcRn chromatography retention time.

It has been found that oxidation had an impact on FcRn binding and could be shown on. FcRn column (see FIG. 6).

It has been shown that the antibody format had no impact on the binding to FcRn column. This was shown for the knob-into-hole format and for several bispecific antibody formats. Thus, the FcRn column can be used for the evaluation of new antibody formats.

In one embodiment the complex is mono-biotinylated.

In one embodiment the chromatography material comprising a non-covalent complex of neonatal Fc receptor (FcRn) and beta-2-microglobulin as ligand has a stability of at least 100 cycles in the methods and uses as reported herein. A cycle is a pH gradient from the first pH value to the second pH value of the respective method or use whereby for regeneration of the material no further change of conditions is required than the final conditions of the method or use. Thus, in one embodiment a cycle is a pH gradient from about pH value pH 5.5 to about pH value pH 8.8.

Figure 7:
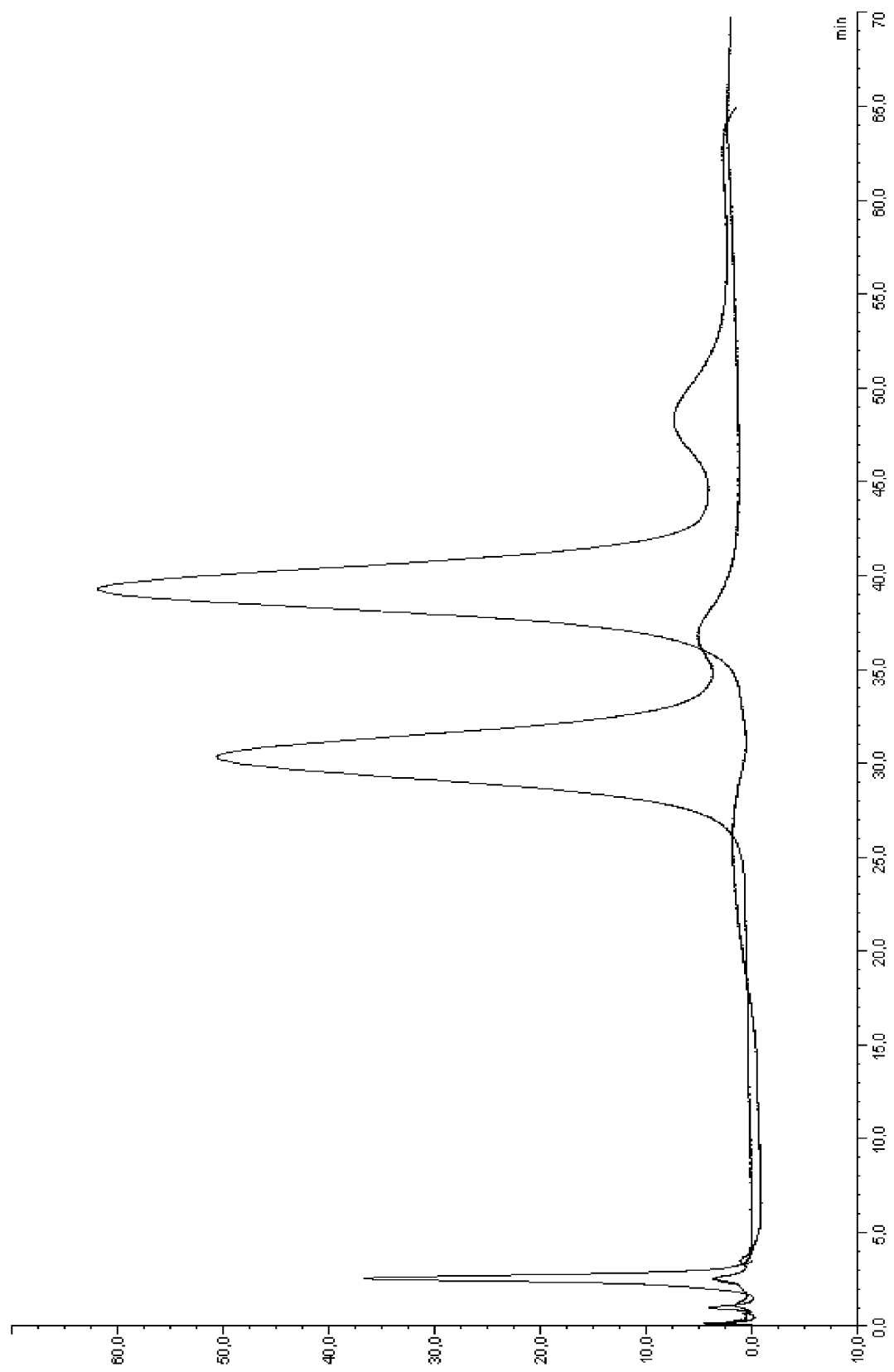
FIG. 7 Chromatogram of anti-Abeta antibody wild-type, and HE-mutant on FcRn column as reported herein.

It has been found that an amino acid exchange from M to H at position 252 in combination with an amino acid exchange M to F at position 428 results in a shortened retention time (see FIG. 7).

The antibody sample with oxidation products Met252 and Met428 illustrates the difference between the SPR technique and the FcRn affinity chromatography. While SPR analysis of the samples detected a relative difference in binding of the sample of about 20% compared with the reference standard, it did not provide insight into the heterogeneity of this sample. In contrast, FcRn affinity chromatography of the same sample displayed two distinct peaks, one at the retention time of the reference standard and the second peak significantly shifted to the left indicating a weaker interaction of the antibody in the stressed sample with the FcRn column material at lower pH.

A chromatography material comprising a non-covalent complex of neonatal Fe receptor (FcRn) and beta-2-microglobulin as ligand as reported herein can be used for the isolation/separation of antibody fragments and, thus, provides for an alternative to conventional Protein A affinity chromatography. In addition by using the chromatography material as reported herein the separation can be effected at more physiological conditions, such as pH value, compared to conventional Protein A affinity chromatography.

The chromatography material comprising a non-covalent complex of neonatal Fc receptor (FcRn) and beta-2-microglobulin as ligand can be used for the determination/separation/enrichment of antibody species comprising modifications such as e.g. oxidation, charge variants, glycosylation, and deamidation. The chromatography material comprising a non-covalent complex of neonatal Fc receptor (FcRn) and beta-2-microglobulin as ligand can be used depending on the chosen pH gradient (start/end pH value) for the enrichment of certain antibody species.

The chromatography material comprising a non-covalent complex of neonatal Fc receptor (FcRn) and beta-2-microglobulin as ligand can be used for the isolation/enrichment of antibodies species by molecular weight variation/difference.

The chromatography material comprising a non-covalent complex of neonatal Fc receptor (FcRn) and beta-2-microglobulin as ligand can be used for the isolation/enrichment of antibodies by the number of FcRn binding site in the molecule.

The chromatography material comprising a non-covalent complex of neonatal Fc receptor (FcRn) and beta-2-microglobulin as ligand can be used for the isolation of amino acid modifications. The chromatography material comprising a non-covalent complex of neonatal Fc receptor (FcRn) and beta-2-microglobulin as ligand can be used for the isolation/separation of bispecific antibody mispairings such as hole-hole dimers and half antibodies.

Specific Embodiment

1. Use of an immobilized non-covalent complex of a neonatal Fc receptor (FcRn) and beta-2-microglobulin (b2m) as affinity chromatography ligand in an affinity chromatography with a positive linear pH gradient.
2. The use according to item 1, characterized in that it is in an affinity chromatography with a positive linear pH gradient for separating antibodies or fusion polypeptides comprising at least an Fc-region.
3. The use according to any one of items 1 to 2, characterized in that the neonatal Fc receptor and the beta-2-microglobulin are independently of each other of human origin, or of mouse origin, or of cynomolgus origin, or of rat origin, or of rabbit.
4. The use according to any one of items 1 to 3, characterized in that the beta-2-microglobulin is from the same species as the neonatal Fc receptor.
5. The use according to any one of items 1 to 4, characterized in that the neonatal Fc receptor and the beta-2-microglobulin are the human wild-type neonatal Fc receptor and the human wild-type beta-2-microglobulin each independently of each other with 0 to 10 amino acid residue modifications.
6. The use according to any one of items 1 to 5, characterized in that the non-covalent complex of a neonatal Fc receptor (FcRn) and beta-2-microglobulin (b2m) is bound to a solid phase.
7. The use according to item 6, characterized in that the solid phase is a chromatography material.
8. The use according to any one of items 6 to 7, characterized in that the non-covalent complex of a neonatal Fc receptor (FcRn) and beta-2-microglobulin (b2m) is biotinylated and the solid phase is derivatized with streptavidin.
9. The use according to any one of items 1 to 8, characterized in that the pH gradient is from a first pH value to a second pH value whereby the first pH value is from about pH 3.5 to about pH 7.5 and the second pH value is from about pH 6.0 to about pH 9.5.
10. The use according, to any one of items 1 to 9, characterized in that the first-pH value is about pH 5.5 and the second pH value is about pH 8.8.
11. The use according to any one of items 1 to 10, characterized in that the use is for the determination of the in vivo half-live of an antibody by determining the ratio of the retention times of the antibody and a reference antibody.
12. The use according to any one of items 1 to 10, characterized in that the use is for determining methionine oxidation of an antibody.
13. The use according to any one of items 1 to 10, characterized in that the use is for determining the oligomerization level of an antibody.
14. The use according to any one of items 1 to 10, characterized in that the use is for screening a library of modified antibodies or modified fusion polypeptides of a parent antibody or a parent fusion polypeptide which comprise at least an FcRn binding portion of an Fc-region for those modified antibodies or modified fusion polypeptides that have an altered binding affinity for FcRn compared to the parent antibody or parent fusion polypeptide.
15. The use according to any one of items 1 to 10, characterized in that the use is for identifying antibodies or fusion polypeptides that comprise at least an FcRn-binding portion of an Fc-region which exhibit altered binding to the neonatal Fc receptor.
16. The use according to any one of items 1 to 10, characterized in that the use is for the removal of half antibodies from IgG preparations.
17. The use according to any one of items 1 to 10, characterized in that the use is for the removal of antibody aggregates and antibody oligomers from IgG preparations.
18. The use according to any one of items 1 to 17, characterized in that the antibody is a monospecific antibody or antibody fragment of fusion polypeptide, or a bispecific antibody or antibody fragment of fusion polypeptide, or a trispecific antibody or antibody fragment of fusion polypeptide, or a tetraspecific antibody or antibody fragment of fusion polypeptide.
19. Use of an immobilized non-covalent complex of a neonatal Fc receptor (FcRn) and beta-2-microglobulin (b2m) as affinity chromatography ligand in an affinity chromatography with a negative linear pH gradient.
20. The use according to item 19, characterized in that it is in an affinity chromatography with a negative linear pH gradient for separating antibodies or fusion polypeptides comprising at least an Fc-region.
21. The use according to any one of items 19 to 20, characterized in that the neonatal Fc receptor and the beta-2-microglobulin are independently of each other of human origin, or of mouse origin, or of cynomolgus origin, or of rat origin, or of rabbit origin.
22. The use according to any one of items 19 to 21, characterized in that the beta-2-microglobulin is from the same species as the neonatal Fc receptor.
23. The use according to any one of items 19 to 22, characterized in that the neonatal Fc receptor and the beta-2-microglobulin are the human wild-type neonatal Fc receptor and the human wild-type beta-2-microglobulin each independently of each other with 0 to 10 amino acid residue modifications.
24. The use according to any one of items 19 to 23, characterized in that the non-covalent complex of a neonatal Fc receptor (FcRn) and beta-2-microglobulin (b2m) is bound to a solid phase.
25. The use according to item 24, characterized in that the solid phase is a chromatography material.
26. The use according to any one of items 24 to 25, characterized in that the non-covalent complex of a neonatal Fc receptor (FcRn) and beta-2-microglobulin (b2m) is biotinylated and the solid phase is derivatized with streptavidin.
27. The use according to any one of items 19 to 26, characterized in that the pH gradient is from a first pH value to a second pH value whereby the first pH value is from about pH 7.0 to about pH 8.5 and the second pH value is from about pH 5.5 to about pH 6.9.
28. The use according to any one of items 19 to 27, characterized in that the first pH value is about pH 7.4 and the second pH value is about pH 6.0.
29. The use according to any one of items 19 to 28, characterized in that the use is for the determination of the in vivo half-live of an antibody by determining the ratio of the retention times of the antibody and a reference antibody.
30. The use according to any one of items 19 to 28, characterized in that the use is for determining methionine oxidation of an antibody.
31. The use according to any one of items 19 to 28, characterized in that the use is for determining the oligomerization level, of an antibody.
32. The use according to any one of items 19 to 28, characterized in that the use is for screening a library of modified antibodies or modified fusion polypeptides of a parent antibody or a parent fusion polypeptide which comprise at least an FcRn binding portion of an Fc-region for those modified antibodies or modified fusion polypeptides that have an altered binding affinity for FcRn compared to the parent antibody or parent fusion polypeptide.
33. The use according to any one of items 19 to 28, characterized in that the use is for identifying antibodies or fusion polypeptides that comprise at least an FcRn-binding portion of an Fc-region which exhibit altered binding to the neonatal Fc receptor.
34. The use according to any one of items 19 to 28, characterized in that the use is for the removal of half antibodies from IgG preparations.
35. The use according to any one of items 19 to 28, characterized in that the use is for the removal of antibody aggregates and antibody oligomers from IgG preparations.
36. The use according to any one of items 19 to 35, characterized in that the antibody is a monospecific antibody or antibody fragment of fusion polypeptide, or a bispecific antibody or antibody fragment of fusion polypeptide, or a trispecific antibody or antibody fragment of fusion polypeptide, or a tetraspecific antibody or antibody fragment of fusion polypeptide.
37. The use according to any one of items 1 to 10, 18, 19 to 28 and 35, characterized in that the use is for the separation of antibodies of the IgG1 subclass from antibodies of the IgG3 subclass.
38. An Fc-region variant of human IgG1 isotype in which the amino acid at position 252 is changed from methionine to histidine and the amino acid at position 428 is changed from methionine to glutamic acid.

1. Antibody Fragments

In certain embodiments, a fusion polypeptide provided herein comprises an antibody fragment. Antibody fragments include, but are not limited to, Fab, Fab', Fab'-SH, F(ab')$_2$, Fv, and scFv fragments, and other fragments described below.

For a review of certain antibody fragments, see Hudson, P. J. et al., Nat. Med. 9 (2003) 129-134. For a review of scFv fragments, see, e.g., Plueckthun, A., In: The Pharmacology of Monoclonal. Antibodies, Vol. 113, Rosenberg and Moore (eds.), Springer-Verlag, New York (1994), pp. 269-315; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J., et al., Nat. Med. 9 (2003) 129-134; and Holliger, P., et al., Proc. Natl. Acad. Sci. USA 90 (1993) 6444-6448. Triabodies and tetrabodies are also described in Hudson. P. J., et al., Nat. Med. 9 (2003) 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1.

Antibody fragments can be made by various techniques, including but not limited to proteolytic digestion of an intact antibody as well as production by recombinant host cells (e.g. *E. coli* or phage), as described herein.

2. Chimeric and Humanized Antibodies

In certain embodiments, an antibody provided herein is a chimeric antibody. Certain chimeric antibodies are described, e.g., in U.S. Pat. No. 4,816,567; and Morrison, S. L., et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and, a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody.

Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al. Proc. Natl. Acad. Sci. USA 86 (1989) 10029-10033; U.S. Pat. Nos. 5,821,337, 7,527,791, 6,982,321, and 7,087,409; Kashmiri, S. V., et al., Methods 36 (2005) 25-34 (describing SDR (a-CDR) grafting); Padlan, E. A., Mol. Immunol. 28 (1991) 489-498 (describing "resurfacing"); Dall'Acqua, W. F., et al., Methods 36 (2005) 43-60 (describing "FR shuffling"); and Osbourn, J., et al., Methods 36 (2005) 61-68 and Klimka, A., et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308; framework regions derived from the consensus sequence of human antibodies of a particular subgroup of light or heavy chain variable regions (see, e.g., Carter, P., et al., Proc. Natl, Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M., et al., J. Biol. Chem. 272 (1997) 10678-10684 and Rosok, M. J., et al., J. Biol. Chem. 271 (1996) 22611-22618).

3. Human Antibodies

In certain embodiments, an antibody provided herein is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125. See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, D., J. Immunol. 133 (1984) 3001-3005; Brodeur, B. R., et al., Monoclonal Antibody Production Techniques and Applications, Marcel Dekker, Inc., New York (1987), pp. 51-63; and Boerner, P., et al., J. Immunol. 147 (1991) 86-95) Human antibodies generated via human B-cell hybridoma technology are also described in Li, S., et al., Proc. Natl. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain.

Techniques for selecting human antibodies from antibody libraries are described below.

4. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R., et al., Methods in Molecular Biology 178 (2002) 1-37 and further described, e.g., in the McCafferty, J., et al., Nature 348 (1990) 552-554; Clarkson, T., et al., Nature 352 (1991) 624-628; Marks, J. D., et al., 3, J. Mol. Biol. 222 (1992) 581-597; Marks, J. D. and Bradbury, A., Methods in Molecular Biology 248 (2003) 161-475; Sidhu, S. S., et al., J. Mol. Biol. 338 (2004) 299-310; Lee, C. V., et al., J. Mol. Biol. 340 (2004) 1073-1093; Fellouse, F. A., Proc. Natl. Acad. Sci. USA 101 (2004) 12467-42472; and Lee, C. V., et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G., et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D., et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example: U.S. Pat. No. 5,750,373, US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

5. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, bispecific antibodies may hind to two different epitopes of the same antigen. Bispecific antibodies may also be used to localize cytotoxic agents to cells which express the antigen. Bispecific antibodies can be prepared as hill length antibodies or antibody fragments.

Techniques for making multispecific antibodies include, but are not limited to, recombinant co-expression of two immunoglobulin heavy chain-light chain pairs having different specificities (see Milstein, C. and Cuellar, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P., et al., Proc. Natl. Acad. Sci. USA 90 (1993) 6444-6448); and using single-chain Fv (sFv) dimers (see, e.g. Gruber, M., et al., J. Immunol. 152 (1994) 5368-5374); and preparing trispecific antibodies as described, e.g., in Tutt, A., et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to different antigens (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/135172, WO 2010/145792, and WO 2010/145793.

6. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Exemplary changes are provided in Table 1 under the heading of "exemplary substitutions", and as further described below in reference to amino acid side chain classes. Conservative substitutions are shown in Table 1 under the heading of "preferred substitutions". Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |

TABLE-continued

| Original Residue | Exemplary Substitutions | Preferred Substitutions |
|---|---|---|
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region (HVR) residues of a parent antibody (e.g. a humanized or human antibody). Generally, the resulting variants) selected for further study will have modifications (e.g., improvements) in certain biological properties (e.g., increased affinity, reduced immunogenicity) relative, to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol, 207 (2008) 179-196), and/or SDRs (a-CDRs), with the resulting variant VH or VL being tested for binding affinity. Affinity maturation by constructing and reselecting from secondary libraries has been described, e.g., in Hoogenboom, H. R., et al., in Methods in Molecular Biology 178 (2002) 1-37, In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A., et al., J. Mol. Biol. 336 (2004) 1239-4249; Yamane-Ohnuki, N., et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y., et al., Biotechnol. Bioeng. 94 (2006) 680-688; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22.764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol, 9 (1991) 457-492. Non-limiting examples of in vitro assays to assess ADCC activity of a molecule of interest is described in U.S. Pat. No. 5,500,362 (see. e.g. Hellstrom, I., et al., Proc. Natl. Acad. Sci. USA 83 (1986) 7059-7063; and Hellstrom, I., et al., Proc. Natl. Acad. Sci. USA 82 (1985) 1499-1502; U.S. Pat. No. 5,821,337 (see Bruggemann, M., et al., S. Exp. Med. 166 (1987) 1351-1364 Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R., et al., Proc. Natl. Acad, Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H., et al., J. Immunol. Methods 202 (1996) 163-171; Cragg, M. S., et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B., et al., Immunol. 18 (2006) 1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called. "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie, E. E., et al., J. Immunol, 164 (2000) 4178-4184.

Antibodies with increased half-lives and improved binding to the neonatal Fc receptor (FcRn), which is responsible for the transfer of maternal IgGs to the fetus (Guyer, R. I., et al., J. Immunol. 117 (1976) 587-593, and Kim, J. K., et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 252, 253, 254, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371, 826).

See also Duncan, A. R. and Winter, G., Nature 322 (1988) 738-740; U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMABs", in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propylene glycol homopolymers, prolylpropylene oxide/ethylene oxide co-polymers, polyoxyethylated polyols (e.g. glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W., et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

III. Recombinant Methods and Compositions

Methods for producing monoclonal antibodies have been reported first by Kohler and Milstein (Nature 256 (1975) 495-497). Thereafter the production of recombinant antibodies with myeloma cells by stably introducing the antibody-encoding nucleic acid (DNA has been reported (see Oi, et al., Proc. Natl. Acad. Sci. USA 80 (1983) 6351-6355).

The encoding nucleic acid of antibodies (either for the complete antibody or for the variable domains) can be isolated and sequenced using conventional procedures from an antibody producing cell. After isolation the encoding nucleic acid can be placed into one or more expression vectors. If only the encoding nucleic acid of the variable domain is isolated the expression vector comprises also a nucleic acid encoding the heavy chain and/or light chain constant region, respectively (see e.g. U.S. Pat. No. 5,658,570). The expression vector can be transfected into prokaryotic (E. coli) or eukaryotic host cells (CHO, HEK, BHK, SP2/0) that do not otherwise secrete antibodies.

If the encoding nucleic acid is derived from a display library, such as a phage display library, a yeast display library, or generally cell surface display library, it can be cloned directly into the expression vector.

Antibodies may be produced using recombinant methods and compositions, e.g., as described in U.S. Pat. No. 4,816,567, in one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody as reported herein is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody as reported herein nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., Methods in Molecular Biology, Vol. 248, Lo, B. K. C. (ed.), Humana Press, Totowa, N.J. (2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H., et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L, et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

III. Immunoconjugates

The invention also provides immunoconjugates comprising an antibody as reported herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and EP 0 425 235 B1); an auristatin such as monomethyl auristatin drug moieties DE and DF (MMAE and MMAF) (see U.S. Pat. Nos. 5,635,483, 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and U.S. Pat. No. 5,877,296; Hinman, L. M., et al, Cancer Res. 53 (1993) 3336-3342; and Lode, H. N., et al., Cancer Res. 58 (1998) 2925-2928); an anthracycline such as daunomycin or doxorubicin (see Kratz, F., et al., Curr. Med. Chem. 13 (2006) 477-523; Jeffrey, S. C., et al., Bioorg. Med. Chem. Lett. 16 (2006) 358-362; Torgov, M. Y., et al., Bioconjug. Chem. 16 (2005) 717-721; Nagy, A., et al Proc. Natl. Acad. Sci. USA 97 (2000) 829-834; Dubowchik, G. M., et al., Bioorg. & Med. Chem. Letters 12 (2002) 1529-1532; King, M. D., et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, Saponaria officinalis inhibitor, gelonin, mitogellin, restrictocin, phenomycin, enomycin, and the tricothecenes.

In other embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $Pb^{32}$, $Pb^{212}$ and radioactive isotopes of Lu. When the radioconjugate is used for detection, it may comprise a radioactive atom for scintigraphic studies, for example $TC^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocynate), and bis-active fluorine compounds (such as 1,5-difluoro-2,4-dinitrobenzene). For example, a ricin immunotoxin can be prepared as described in Vitetta, E. S., et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V., et al., Cancer Res. 52 (1992) 127-131; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SPAP, SIA, SIAB, SMCC, SMPB, SMPH, sulfo-EMCS, sulfo-GMBS, sulfo-KMUS, sulfa-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

IV. Methods and Compositions for Diagnostics and Detection

In certain embodiments, any of the antibodies provided herein is useful for detecting the presence of its antigen in a biological sample. The term "detecting" as used herein encompasses quantitative or qualitative detection. In certain embodiments, a biological sample comprises a cell or tissue.

In one embodiment, an antibody as reported herein for use in a method of diagnosis or detection is provided. In a further aspect, a method of detecting the presence of an antigen in a biological sample is provided. In certain embodiments, the method comprises contacting the biological sample with an antibody as described herein under conditions permissive for binding of the antibody to its antigen, and detecting whether a complex is formed between the antibody and the antigen. Such method may be an in vitro or in vivo method.

In certain embodiments, labeled antibodies as reported herein are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

V. Pharmaceutical Formulations

Pharmaceutical formulations of an antibody as described herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulation or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter international, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose tar gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

VI. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an antibody as reported herein.

The following examples, figures and sequences are provided to aid the understanding of the present invention, the true scope of which is set forth in the appended claims. It is understood that modifications can be made in the procedures set forth without departing from the spirit of the invention.

Examples

Methods

Electrospray Ionization Mass Spectometry (ESI-MS)

Protein aliquots (50 µg) were deglycosylated by adding 0.5 µN-Glycanase plus (Roche) and sodium phosphate buffer (0.1 M, pH 7.1) to obtain a final sample volume of 115 µL. The mixture was incubated at 37° C. for 18 h. Afterwards for reduction and denaturing 60 µL 0.5 TCEP (Pierce) in 4 M guanidine*HCl (Pierce) and 50 µL 8 M guanidine*HCl were added. The mixture was incubated at 37° C. for 30 min. Samples were desalted by size exclusion chromatography (Sepharose G-25, isocratic, 40% acetonitrile with 2% formic acid). ESI mass spectra (+ve) were recorded on a Q-TOF instrument (maXis, Bruker) equipped with a nano ESI source (TriVersa NanoMate, Advion). MS parameter settings were as follows: Transfer: Funnel RF, 400 Vpp; ISCID Energy, 0 eV; Multipole RF, 400 Vpp; Quadrupole: Ion Energy, 4.0 eV; Low Mass, 600 m/z; Source: Dry Gas, 8 L/min; Dry Gas Temperature, 160° C.; Collision Cell: Collision Energy, 10 eV; Collision RF: 2000 Vpp; Ion Cooler: Ion Cooler RF, 300 Vpp; Transfer Time: 120 µs; Pre Puls Storage, 10 µs; scan range m/z 600 to 2000. For data evaluation in-house developed software (MassAnalyzer) was used.

FcRn Surface Plasmon Resonance (SPR) Analysis

The binding properties of wild-type antibody and the mutants to FcRn were analyzed by surface plasmon resonance (SPR) technology using a BIAcore T100 instrument (BIAcore AB, Uppsala, Sweden). This system is well established for the study of molecular interactions. It allows a continuous real-time monitoring of ligand/analyte bindings and thus the determination of kinetic parameters in various assay settings SPR-technology is based on the measurement of the refractive index close to the surface of a gold coated biosensor chip. Changes in the refractive index indicate mass changes on the surface caused by the interaction of immobilized ligand with analyte injected in solution. If molecules bind to an immobilized ligand on the surface the mass increases, in case of dissociation the mass decreases. In the current assay, the FcRn receptor was immobilized onto a BIAcore CM5-biosensor chip (GE Healthcare Bioscience, Uppsala, Sweden) via amine coupling to a level of 400 Response units (RU). The assay was carried out at room temperature with PBS, 0.05 Tween20 pH 6.0 (GE Healthcare Bioscience) as running and dilution buffer. 200 nM of native or oxidized antibody samples were injected at a flow rate of 50 µL/min at room temperature. Association time was 180 s, dissociation phase took 360 s. Regeneration of the chip surface was reached by a short injection of HBS-P, pH 8.0. Evaluation of SPR-data was performed by comparison of the biological response signal height at 180 s after injection and at 300 s after injection. The corresponding parameters are the RU max level (180 s after injection) and late stability (300 s after end of injection).

Example 1

Preparation of FcRn Affinity Column
Expression of FcRn in HEK293 cells

FcRn was transiently expressed by transfection of HEK293 cells with two plasmids containing the coding sequence of FcRn and of beta-2-microglobulin. The transfected cells were cultured in shaker flasks at 36.5° C., 120 rpm (shaker amplitude 5 cm), 80% humidity and 7% $CO_2$. The cells were diluted every 2-3 days to a density of 3 to $4*10^5$ cells/ml.

For transient expression, a 14 l stainless steel bioreactor was started with a culture volume of 8 l at 36.5° C., pH 7.0±0.2, $pO_2$ 35% (gassing with $N_2$ and air, total gas flow 200 ml $min^{-1}$) and a stirrer speed of 100-400 rpm. When the cell density reached $200*10^5$ cells/ml, 10 mg plasmid DNA (equimolar amounts of both plasmids) was diluted in 400 ml Opti-MEM (Invitrogen). 20 ml of 293fectin (Invitrogen) was added to this mixture, which was then incubated for 15 minutes at room temperature and subsequently transferred into the fermenter. From the next day on, the cells were supplied with nutrients in continuous mode: a feed solution was added at a rate of 500 ml per day and glucose as needed to keep the level above 2 g/l. The supernatant was harvested 7 days after transfection using a swing head centrifuge with 1 l buckets: 4000 rpm for 90 minutes. The supernatant (13 L) was cleared by a Sartobran P filter (0.45 µm+0.2 µm, Sartorius) and the FcRn beta-2-microglobulin complex was purified therefrom.

Biotinylation of Neonatal Fc Receptor

A soluble extracellular domain of FcRn with His-Avi Tag that has been co-expressed with $\beta_2$-microglobulin in HEK293 cells was biotinylated after purification as follows:

Between 1.2 mg and 12 mg FcRn/$\beta_2$-microglobulin in 5 ml 20 mM sodium citrate buffer, pH 5.5 containing 150 mM KCl, 250 µl PBS and 1 tablet Complete protease inhibitor (Roche Diagnostics GmbH, Mannheim, Germany) were biotinylated using the biotinylation kit from Avidity according to the manufacturer instructions (Bulk BIRA). Biotinylation reaction was done at room temperature overnight. The modified protein was dialyzed against 20 mM sodium phosphate buffer comprising 150 mM NaCl, pH 7.5 at 4° C. over night to remove excess of biotin.

Coupling to Streptavidin Sepharose

One gram streptavidin sepharose (GE Healthcare) was added to the biotinylated and dialyzed receptor (between 1.2 and 12 mg FcRn/β2-microglobulin, for standard analytical application 3 mg were chosen) and incubated for two hours with shaking. The receptor derivatized sepharose was filled in a 1 ml XK column (GE Healthcare).

Example 2

Chromatography Using the FcRn Affinity Column

The receptor derivatized sepharose was filled in a 1 ml XK column (GE Healthcare) and the FcRn column then was equilibrated with 20 mM 2-(N-morpholine)-ethanesulfonic acid (MES) buffer containing 150 mM NaCl, pH 5.5.

Conditions:

column dimensions: 50 mm×5 mm bed height: 5 cm loading: 50 µg sample equilibration buffer: 20 mM MES, with 150 mM NaCl, adjusted to pH 5.5 elution buffer: 20 mM Tris/HCl, with 150 mM NaCl, adjusted to pH 8.8 elution: 7.5 CV equilibration buffer, in 30 CV to 100% elution buffer, 10 CV elution buffer Antibody or fusion protein samples containing 50 to 100 µg of protein were adjusted to pH 5.5 and applied to the FcRn column using ÄKTA explorer 10 XT or Dionex Summit (Dionex, Idstein, Germany). The column with 5 cm bed height was then washed with 5-10 column volumes of equilibration buffer 20 mM MES, 150 mM NaCl, pH 5.5. The affinity-bound Fc-containing proteins were eluted with a pH gradient to 20 mM Tris/HCl, 150 mM NaCl, pH 8.8, in 30 column volumes. For complete elution of modified antibodies, the pH was increased in the gradient up to pH 8.8. The experiments were carried out at room temperature. The elution profile was obtained by continuous measurement of the absorbance at 280 nm. The time taken for an analyte peak, X, to reach the detector after sample injection was called the retention time.

Example 3

Correlation of Retention Time on FcRn Column to In Vivo Half Life

In vivo half-life was measured in human FcRn transgenic C57BL/6J mice after single i.v. admin. of 10 mg/kg (n=8) and compared to the retention time on the Fc column (see table). It was found that antibodies that showed a late elution from the FcRn column had a longer half-life in FcRn transgenic mice.

TABLE

| antibody | retention time [min] | in vivo half-life [h] |
| --- | --- | --- |
| anti-Abeta antibody (wild-type) | 45.5 | 103 +/− 51 |
| anti-Abeta antibody (YTE-mutation) | 52.5/66 | 197 +/− 53 |
| anti-IGF-1R antibody (wild-type) | 45.5 | 97 +/− 9 |
| anti-IGF-1R antibody (YTE-mutant) | 58 | 211 +/− 41 |

Example 4

Purification of Human FcRn, Mouse FcRn and Cynomolgus FcRn

The clarified supernatants containing hexahis-tagged proteins were loaded on a Ni-NTA affinity chromatography resin (Qiagen, Harbrechtikon, Switzerland) at 4° C. After wash steps with 20 mM sodium phosphate buffer comprising 500 mM NaCl at pH 7.4 and containing 20 mM, respectively 100 mM imidazole, proteins were eluted at a flow rate of 2 ml/min using batch elution with the same buffer containing 300 mM imidazole on an ÄKTA Prime chromatography system (Amersham Pharmacia Biotech, Uppsala, Sweden). Fractions were pooled and further purified in sodium phosphate buffer containing 500 mM NaCl on size exclusion chromatography (Superdex™ 200, GE Healthcare, Zurich, Switzerland). Purified proteins were quantified using a Nanodrop spectrophotometer (Nanodrop Technologies, Wilmington, Del.) and analyzed by SDS PAGE on NuPAGE 4-12% Bis-Tris gels in MES buffer under denaturing and reducing conditions.

Example 5

Mouse and Cynomolgus FcRn Affinity Column Chromatographies

In the following table retention times of exemplary human antibodies on affinity columns comprising FcRn from Cynomolgus monkey are given. Data were obtained using the following conditions: Elution buffer: 20 mM TRIS/HCl, 150 mM NaCl, pH 8.5. Further description: see Example 2. The term YTE-mutant denotes the triple mutant M252Y/S254T/T256E.

| antibody | retention time [min] |
| --- | --- |
| anti-Abeta antibody (wild-type) | 48.8 |
| anti-Abeta antibody (YTE-mutant) | 57.4 |
| anti-IGF-1R antibody (wild-type) | 51.2 |
| anti-IGF-1R antibody (YTE-mutant) | 63.0 |

In the following Table retention times of exemplary human antibodies on murine FcRn are given. Data were obtained using the following conditions: 1.2 mg receptor coupled on 1 ml Sepharose. Elution buffer: 20 mM TRIS/HCl, 150 mM NaCl, pH 8.5. Further description: see Example 2. The YTE-mutants are not included in this table as they could not have been eluted unless the pH of the elution buffer had been adjusted to 9.5.

| antibody | retention time [min] |
| --- | --- |
| anti-Abeta antibody (wild-type) | 54.7 |
| anti-IGF-1R antibody (wild-type) | 48.8 |

Cynomolgus FcRn affinity column behaves similar as human FcRn affinity column concerning binding of humanized antibodies. On the other hand binding of humanized antibodies to murine FcRn column is stronger than to human FcRn affinity column as can be seen by later retention.

Example 6

Generation of Antibody Fragments

The F(ab'))$_2$ fragment and the Fc-region fragment were prepared by cleavage of the full-length antibody 1:1 diluted with 100 mM Tris, pH 8.0, by adding 1 μg IdeS cysteine protease per 50 μg antibody and incubation for 2 h at 37° C. The resulting cleavage products F(ab')$_2$ and Fc were separated on a size exclusion chromatography (SEC) column (Superdex 200, GE Healthcare, Zurich, Switzerland) using an ÄKTA Explorer chromatography system (GE Healthcare, Uppsala, Sweden) and the peak fractions were pooled. Molecular weight standards on the same column served to identify the two cleavage products based on their retention times.

Retention times of full-length antibodies varied notably. In contrast, the retention times of the respective Fc portions of all tested antibodies virtually did not differ from each other (<1%).

When plasmin was used for cleavage of the full-length antibodies, the same findings were obtained (data not shown).

Example 7

Correlation of Retention Time on FcRn Column to Oxidation State

The influence of oxidation of the antibody on the retention time in the FcRn affinity chromatography was studied. Oxidation of an IgG1 antibody (1 mg/ml) was observed by storing the antibody at 40° C. for 2 months. The unmodified and the oxidized antibody samples were analyzed by FcRn affinity chromatography and by FcRn surface plasmon resonance (SPR) technology. Oxidation of the antibody was characterized by peptide mapping—and electrospray ionization mass spectrometry (ESI-MS).

Figure 8:
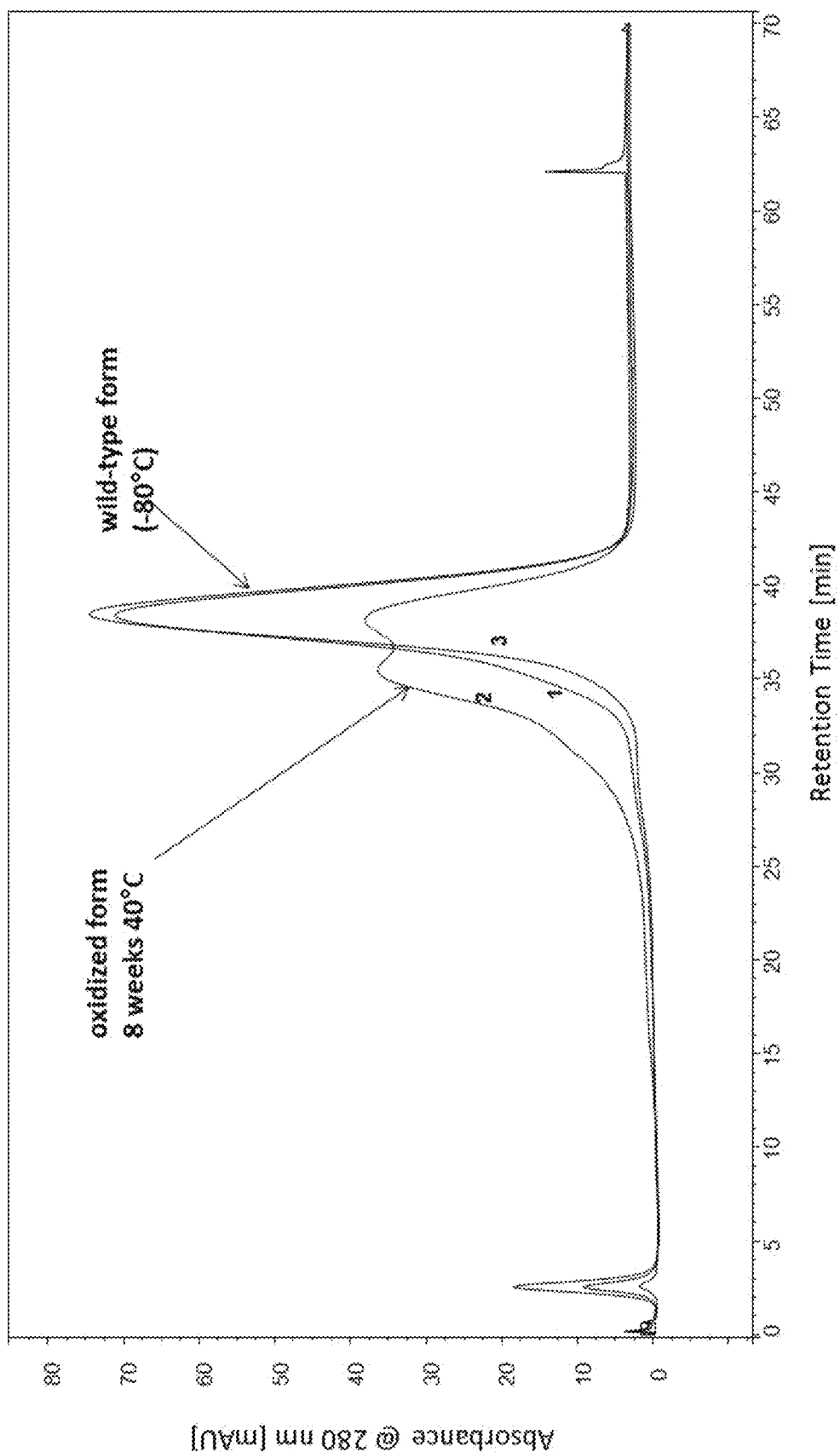
FIG. 8 Impact of Met252 and Met428 oxidation on FcRn interaction. Application of a sample of an IgG1 antibody stored for 2 months at 40° C. (curve 2) to the FcRn column leads to an earlier eluting species with a double peak indicative of oxidized IgG1 antibody while application of samples of IgG1 antibody stored for 2 months at 25° C. (curve 1) and −80° C. (curve 3) to the FcRn column leads to later eluting, virtually overlapping peaks. Chromatography conditions: buffer A (20 mM MES, 150 mM NaCl, pH 5.5), buffer B (20 mM HEPES, 150 mM NaCl, pH 8.2), flow 0.5 ml/min, gradient from buffer A to buffer B: 60 min. (standard).
Figure 9:
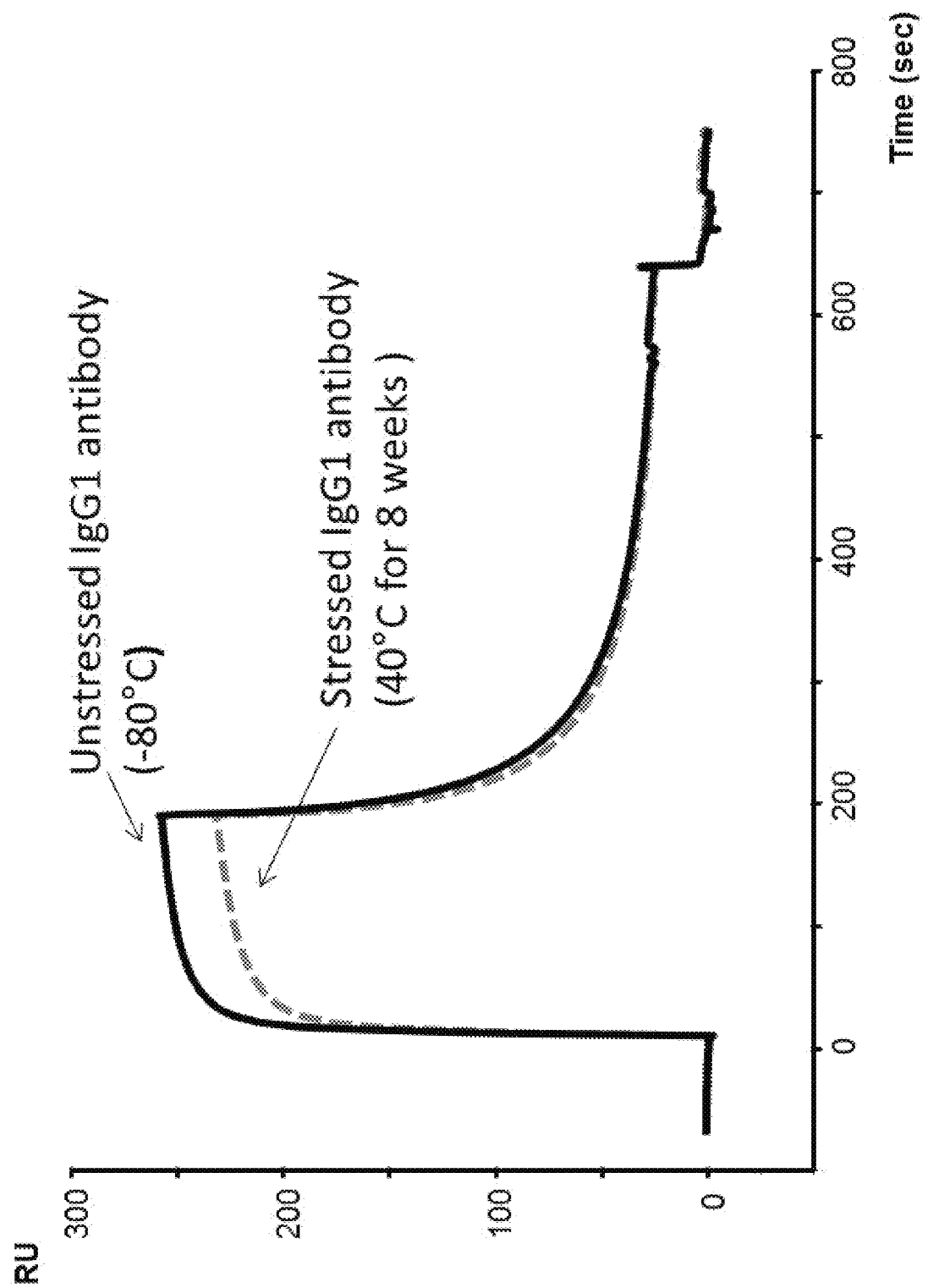
FIG. 9 Surface plasmon resonance (SPR) analysis of stressed IgG1 antibody. Application of a sample of the IgG1 antibody stored for 2 months at 40° C. to the BIAcore for SPR analysis shows different sensorgrams for wild-type and for Met252 and Met428 oxidized IgG1 antibody species.

ESI-NIS data revealed that approximately 50% of heavy chains of the IgG1 antibody were oxidized at the solvent exposed Met252 and Met428 residues upon storage in buffer (20 mM His/His*HCl, 240 mM Trehalose, 0.02% polysorbate 20) under accelerated conditions at 40° C. for two months. When samples stressed at 40° C. containing oxidized antibody and samples stored at −80° C. and at 25° C. were applied to an affinity column on which FcRn previously was immobilized, two major peaks could be separated (FIG. 8). The second peak of FIG. 8 consisting of two virtually overlapping curves with longer retention time corresponded to the elution time of the unmodified antibody in samples stored at 25° C. and at −80° C. while the earlier eluting peak represented Met252 and Met428 oxidized antibody. The presence of oxidized Met252 and Met428 was supported by the 16 Da mass shift detected in the stressed sample by ESI-MS. Analysis of the stressed (40° C.) antibody sample by SPR in the BIAcore showed the same response pattern in the sensorgram as in the FcRn chromatography with two different antibody species, i.e. wild-type antibody and Met252- and Met428-oxidized antibody (FIG. 9).

Example 8

Correlation of Retention Time on FcRn Column to Aggregate Formation

The influence of antibody aggregate formation on FcRn interaction in the affinity chromatography was evaluated for an anti-IL13Ralpha antibody. The antibody monomer and aggregate fractions were isolated by size exclusion chromatography (SEC) and pooling of the respective peaks. The FcRn interaction of the fractions was analyzed by affinity chromatography and by SPR technology.

Figure 10:
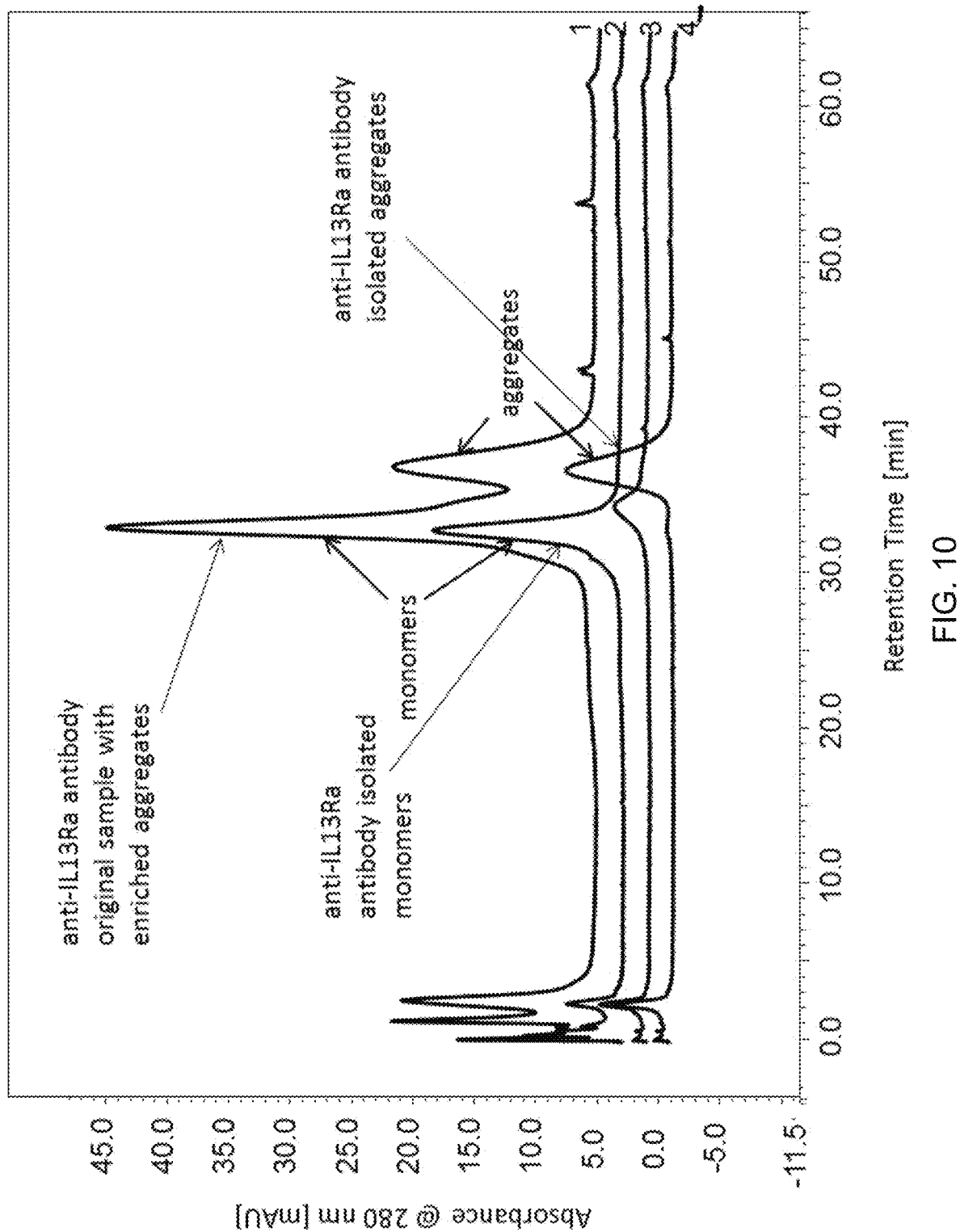
FIG. 10 Impact of antibody aggregates on FcRn interaction. FcRn chromatographic analysis of anti-IL13Ralpha antibody in the original sample, its isolated monomers and isolated aggregates. Chromatography conditions: buffer A (20 mM MES, 150 mM NaCl, pH 5.5), buffer B (20 mM Tris/HCl, 150 mM NaCl, pH 8.8), flow 0.5 mL/min, gradient from buffer A to buffer B: 50 min (standard).

Size exclusion chromatography (SEC) was used to isolate three anti-IL13Ralpha antibody fractions containing anti-IL13Ralpha antibody monomers and multimeric aggregates for the FcRn column chromatography. Based on the peak areas of the chromatogram, the sample of anti-IL1.3Ralpha antibody used for FcRn affinity chromatography contained 57% monomers and 43% aggregates of anti-IL13Ralpha antibody. Analysis of the unfractionated sample in the FcRn affinity chromatography revealed two major peaks with different retention times (FIG. 10). The smaller peak with a longer retention time corresponded to that of the aggregate fraction while the major part of the faster eluting peak corresponded to the monomer fraction.

In the surface plasmon resonance (SPR) analysis, an anti-IL13Ralpha antibody reference standard was compared with two different pooled fractions enriched for aggregates (pool 1) and for monomers (pool 2) and with the native pool. The exact composition of the native batch and pooled fractions is described in the following Table.

TABLE

Composition of native and enriched pooled fractions of an anti-IL13Ralpha antibody.

|  | monomers [%] | Fc-dimers [%] | aggregates [%] |
|---|---|---|---|
| starting pool | 91.0 | 8.6 | 0.4 |
| pool 1 | 27.7 | 26.9 | 45.4 |
| pool 2 | 98.3 | 1.4 | 0.4 |

Figure 11:
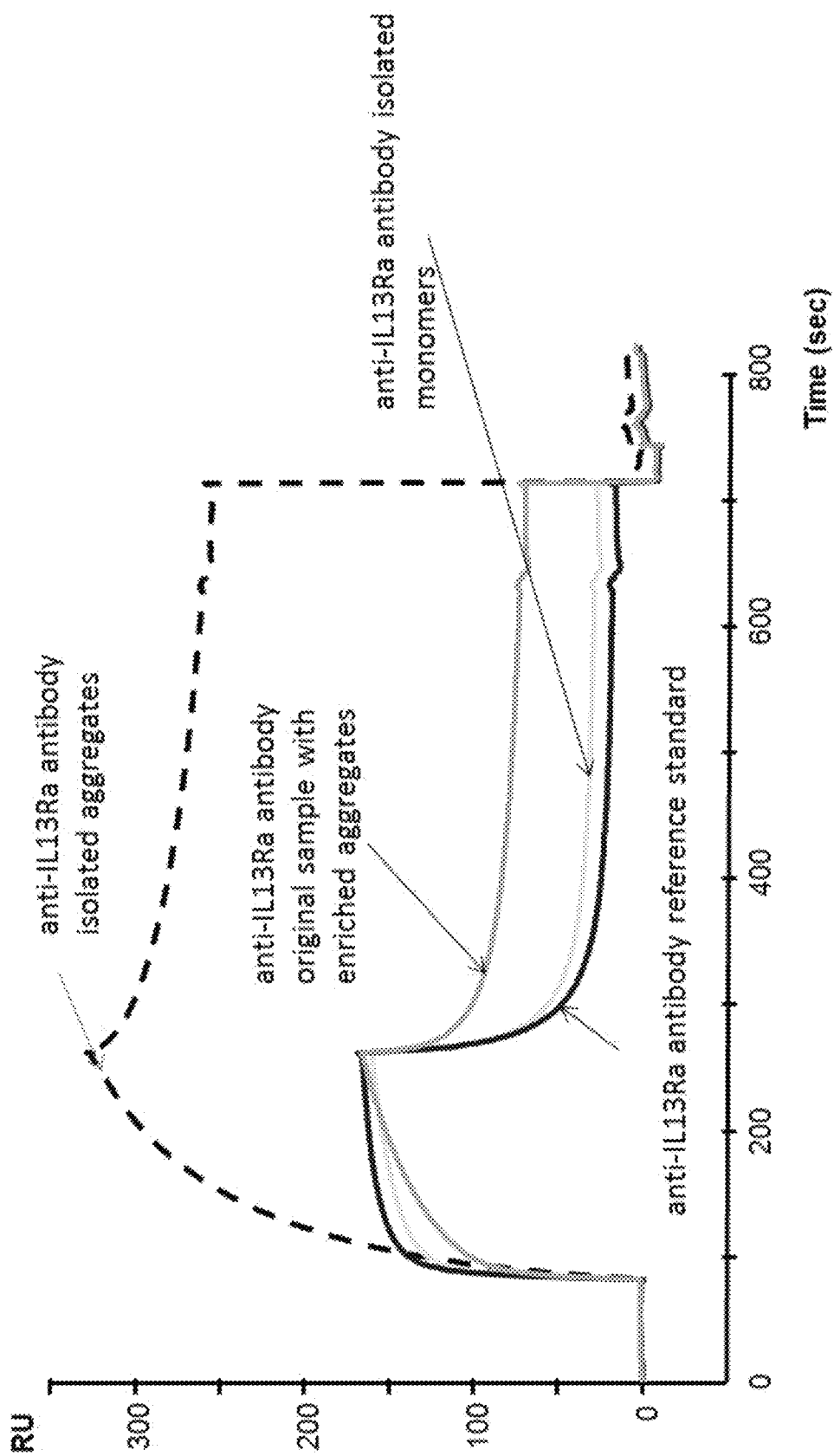
FIG. 11 SPR analysis of anti-IL13Ralpha antibody aggregates. Sensorgrams of anti-IL13Ralpha antibody as reference standard (curve 1), in the original sample (3), of isolated anti-IL13Ralpha antibody monomers (curve 2) and isolated anti-IL13Ralpha antibody aggregates (curve 4).

The sensorgram of the monomer-enriched pool 2 sample was closest to that of the anti-IL13Ralpha antibody reference standard followed by the sensorgram of the aggregate-poor sample. In contrast, the aggregate-enriched pool 1 was characterized by a nearly twice as high binding to FcRn in the SPR analysis (FIG. 11).

Example 9

Pharmacokinetic Study in Human FcRn Mice

All procedures were carried out M accordance with the guidelines of the Association for Assessment and Accreditation of Laboratory Animal Care (www.aaalac.org). The study was authorized by the Regional Council of Oberbayern, Germany.

Male and female C57BL/6J mice (background); mouse FcRn deficient, but hemizygous transgenic for human FcRn (huFcRn (276) −/tg (30, 31) were used throughout the pharmacokinetic study.

At the time of administration, the animals weighed between 17 and 25 g. The respective antibody was given as a single intravenous bolus injection via the tail vein. Due to limited blood volume of mice, three groups of four male and four female animals each were required to cover nine sampling time points, i.e. three sampling time points per animal. Blood samples were taken in group 1 at 5 min, 24 hours and 336 hours, in group 2 at 2 hours, 168 hours and 504 hours and in group 3 at 8 hours, 48 hours and 672 hours after administration. Blood samples of about 100 µL were obtained by retrobulbar puncture and stored at room temperature for 60 min. to allow clotting. Serum samples of at least 40 µL were obtained by centrifugation at 9,300×g at 4° C. for 3 min and immediately frozen and stored at −20° C. until assayed.

Serum concentrations of the human therapeutic antibodies in murine serum were determined by an antigen-captured enzyme linked immunosorbent assay (ELISA specific for the antigen binding region (Fab) of the administered antibody and its variants. All reagents or samples were incubated at room temperature on a shaker at 400 rpm. Each washing step included three cycles. Briefly, streptavidin-coated microtiter plates were coated with biotinylated antibody diluted in assay buffer. After washing with phosphate-buffered saline-polysorbate 20 (Tween20), serum samples in various dilutions were added and incubated for 1 h. After washing, bound human therapeutic antibodies were detected by subsequent incubation with human Fcγ-specific monoclonal antibody Fab fragments conjugated with digoxigenin that do not cross react with mouse IgG. After washing, an anti-digoxigenin antibody conjugated with horseradish peroxidase (HRP) was added and incubated for 1 h. After washing, ABTS (2,2'Azino-di[3-ethylbenzthiazoline sulfonate; Roche Diagnostics, Germany) was added as HRP substrate to form a colored reaction product. Absorbance of the resulting reaction product was read at 405 DM with a reference wavelength at 490 nm. All serum samples and positive or negative control samples were analyzed in replicates and calibrated against reference standard.

The pharmacokinetic parameters were calculated by non-compartmental analysis, using the pharmacokinetic evaluation program WinNonlin™ (Pharsight, St. Louis, Mo., USA), version 5.2.1. Briefly, the area under the concentration/time curve AUC(0-672) was calculated by linear trapezoidal rule (with linear interpolation) from time 0 to infinity. The apparent terminal half-life ($T_{1/2}$) was derived from the equation: $T_{1/2} = \ln 2/\lambda z$. Total body clearance (CL) was calculated as dose/AUC. Statistically significant differences in the pharmacokinetic parameters between the wild-type antibody and its variants were determined by ANOVA analysis.

Figure 12:
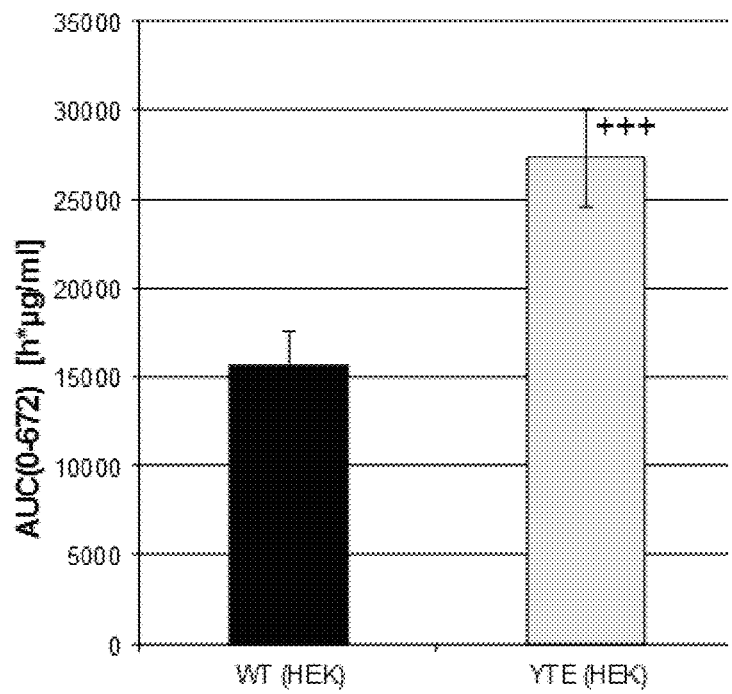
FIG. 12 Impact of Fc mutations on pharmacokinetics in FcRn transgenic mice. Wild-type antibody or its triple mutant YTE were given as a single i.v. bolus injection of 10 mg/kg to 8 animals per group. Results are presented as the mean±standard deviation (SD), ANOVA analysis of significance in comparison with wild-type antibody (+++, p<0.001). A: Area under the serum concentration-time curve from time 0 to 672 h (AUC(0-672)). B: Terminal half-life.
Figure 12:
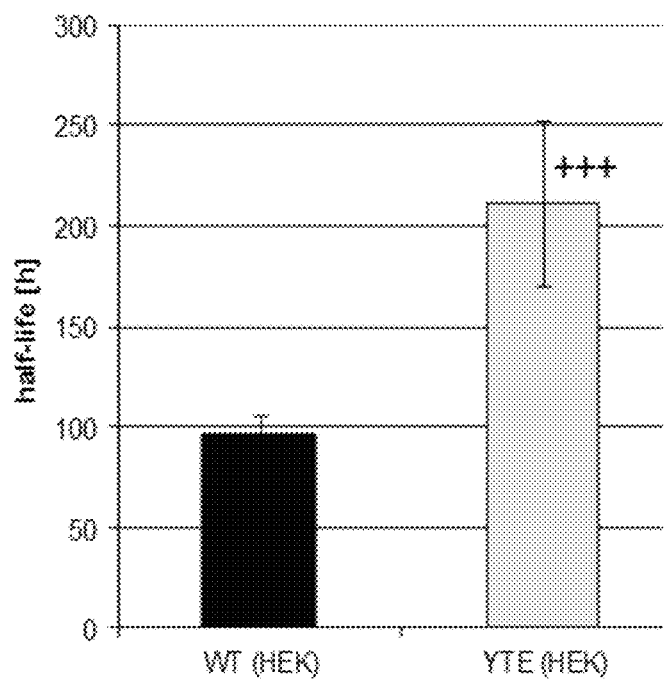

The pharmacokinetic study in C57BL/6J mice deficient for mouse FcRn, but hemizygous transgenic for human FcRn (huFcRn (276) −/tg) showed that the YTE mutation enhanced pharmacokinetics of the antibody (FIG. 12). At a level of statistical significance, the YTE mutant had a 1.74-fold higher AUC(0-672), 1.95-fold slower clearance and a 2.2-fold longer terminal half-life in comparison with wild-type antibody (Table).

TABLE

Pharmacokinetic parameters for wild-type antibody and its triple mutant YTE obtained by non-compartmental analysis of serum concentration measured by ELISA after a single i.v. bolus injection of 10 mg/kg to human FcRn transgenic mice. Mean ± SD, n = 8 per group, ANOVA analysis of significance in comparison with wild-type antibody (+++, p < 0.001). AUC(0-672), area under the serum concentration-time curve from time 0 to 672 h.

| antibody | AUC(0-672) [h*µg/ml] | clearance [ml/min/kg] | terminal half-life [h] |
|---|---|---|---|
| wild-type antibody | 15.693 ± 1.879 | 0.0107 ± 0.0013 | 96.8 ± 8.9 |
| YTE-mutant | 27.359 ± 2.731 | 0.0055 ± 0.0006 | 211.4 ± 40.6 |

The invention claimed is:

1. A method for screening a library of modified antibodies or modified fusion polypeptides of a parent antibody or a parent fusion polypeptide which comprise at least an FcRn binding portion of an Fc-region for those modified antibodies or modified fusion polypeptides that have an altered binding affinity for FcRn compared to the parent antibody or parent fusion polypeptide on an FcRn affinity column comprising a non-covalent complex of neonatal Fc receptor (FcRn) and beta-2-microglobulin as ligand with a positive linear pH gradient, wherein the non-covalent complex is conjugated to biotin and immobilization to a solid support is performed via solid support immobilized avidin, and wherein the complex is mono-biotinylated, said method comprising the steps of:
   (a) applying the individual members of the library and the parent antibody or parent fusion polypeptide to the FcRn affinity chromatography column;
   (b) recovering the individual members of the library with a linear positive pH gradient and determining the individual retention times; and
   (c) selecting those antibodies or fusion polypeptides that have altered binding affinity for FcRn compared to the parent antibody or parent fusion polypeptide,
   wherein the neonatal Fc receptor has an amino acid sequence of SEQ ID NO: 07 with C-terminal His-Avi-tag of SEQ ID NO: 08.

2. The method according to claim 1, wherein the neonatal Fc receptor and the beta-2-microglobulin are independently of each other of human origin, or of mouse origin, or of cynomolgus origin, or of rat origin, or of rabbit origin.

3. The method according to claim 1, wherein the beta-2-microglobulin is from the same species as the neonatal Fc receptor.

4. The method according to claim 1, wherein the neonatal Fc receptor and the beta-2-microglobulin are the human wild-type neonatal Fc receptor and the human wild-type beta-2-microglobulin each independently of each other with 0 to 10 amino acid residue modifications.

5. The method according to claim 1, wherein the non-covalent complex of a neonatal Fc receptor (FcRn) and beta-2-microglobulin (b2m) is bound to a solid phase.

6. The method according to claim 1, wherein the positive linear pH gradient is from a first pH value to a second pH value whereby the first pH value is from about pH 3.5 to about 7.5 and the second pH value is from about pH 6.0 to about pH 9.5.

7. The method according to claim 1, wherein the positive linear pH gradient is from about pH 5.5 to about pH 8.8.

8. The method according to claim 1, wherein the antibody is a monospecific antibody or antibody fragment of fusion polypeptide, or a bispecific antibody or antibody fragment of fusion polypeptide, or a trispecific antibody or antibody fragment of fusion polypeptide, or a tetraspecific antibody or antibody fragment of fusion polypeptide.

9. A method for identifying antibodies or fusion polypeptides that comprise at least an FcRn-binding portion of an Fc-region which exhibit altered binding to the neonatal Fc receptor on an Ran affinity column comprising a non-covalent complex of neonatal Fc receptor (FcRn) and beta-2-microglobulin as ligand with a positive linear pH gradient, said method comprising the steps of:

(a) applying a variant antibody comprising an at least an FcRn-binding portion of an Fc-region, wherein one or more of the following amino acid residues according to the EU numbering of Kabat are altered F243, P244, P245 P, K246, P247, K248, D249, T250, L251, M252, I253, S254, R255, T256, P257, E258, V259, T260, C261, F275, N276, W277, Y278, V279, D280, V282, E283, V284, H285, N286, A287, K288, T289, K290, P291, R292, E293, V302, V303, S304, V305, L306, T307, V308, L309, H310, Q311, D312, W313, L314, N315, G316, K317, E318, Y319, I336, S337, K338, A339, K340, G341, Q342, P343, R344, E345, P346, Q347, V348, C367, V369, F372, Y373, P374, S375, D376, I377, A378, V379, E380, W381, E382, S383, N384, G385, Q386, P387, E388, N389, Y391, T393, S408, S424, C425, S426, V427, M428, H429, E430, A431, L432, H433, N434, H435, Y436, T437, Q438, K439, and S440, and the parent antibody to the FcRn affinity chromatography column;

(b) recovering the variant and the parent antibody with a positive linear pH gradient and determining the individual retention times; and (c) identifying the variant antibody to have altered binding affinity for FcRn compared to the parent antibody if the variant antibody has a different retention time, wherein the neonatal Fc receptor has an amino acid sequence of SEQ ID NO: 07 with C-terminal His-Avi-tag of SEQ ID NO: 08.

10. The method according to claim 9, wherein the neonatal Fc receptor and the beta-2-microglobulin are independently of each other of human origin, or of mouse origin, or of cynomolgus origin, or of rat origin, or of rabbit origin.

11. The method according to claim 9, wherein the beta-2-microglobulin is from the same species as the neonatal Fc receptor.

12. The method according to claim 9, wherein the neonatal Fc receptor and the beta-2-microglobulin are the human wild-type neonatal Fc receptor and the human wild-type beta-2-microglobulin each independently of each other with 0 to 10 amino acid residue modifications.

13. The method according to claim 9, wherein the non-covalent complex of a neonatal Fc receptor (FcRn) and beta-2-microglobulin (b2m) is bound to a solid phase.

14. The method according to claim 9, wherein the positive linear pH gradient is from a first pH value to a second pH value whereby the first value is from about pH 3.5 to about pH 7.5 and the second pH value is from about pH 6.0 to about pH 9.5.

15. The method according to claim 9, wherein the positive linear pH gradient is from about pH 5.5 to about pH 8.8.

16. The method according to claim 9, wherein the antibody is a monospecific antibody or antibody fragment of fusion polypeptide, or a bispecific antibody or antibody fragment of fusion polypeptide, or a trispecific antibody or antibody fragment of fusion polypeptide, or a tetraspecific antibody or antibody fragment of fusion polypeptide.

* * * * *

UNITED STATES PATENT AND TRADEMARK OFFICE
CERTIFICATE OF CORRECTION

PATENT NO. : 11,814,409 B2
APPLICATION NO. : 16/258294
DATED : November 14, 2023
INVENTOR(S) : Roberto Falkenstein et al.

It is certified that error appears in the above-identified patent and that said Letters Patent is hereby corrected as shown below:

In the Claims

At Column 60, Line 51, --pH-- should be inserted before "7.5 and the second pH value."

At Column 60, Line 64, "Ran" should be printed as "FcRn."

At Column 62, Line 17, "whereby the first value" should be printed as "whereby the first pH value."

Signed and Sealed this
Second Day of January, 2024

Katherine Kelly Vidal
*Director of the United States Patent and Trademark Office*